US010731013B2

(12) United States Patent
Foo et al.

(10) Patent No.: US 10,731,013 B2
(45) Date of Patent: Aug. 4, 2020

(54) ELASTOMERIC ARTICLES, COMPOSITIONS, AND METHODS FOR THEIR PRODUCTION

(71) Applicant: SKINPROTECT CORPORATION SDN BHD, Kuala Lumpur (MY)

(72) Inventors: Khon Pu Foo, Selangor (MY); Kumaresan Prabhakaran, Kuala Lumpur (MY)

(73) Assignee: SKINPROTECT CORPORATION SDN BHD, Kuala Lumpur (MY)

(*) Notice: Subject to any disclaimer, the term of this patent is extended or adjusted under 35 U.S.C. 154(b) by 0 days.

(21) Appl. No.: 15/142,707

(22) Filed: Apr. 29, 2016

(65) Prior Publication Data

US 2017/0218143 A1  Aug. 3, 2017

(30) Foreign Application Priority Data

Jan. 29, 2016 (AU) .................. 2016900326
Jan. 29, 2016 (AU) .................. 2016900327

(51) Int. Cl.
| *C08J 5/02* | (2006.01) |
| *A61B 42/10* | (2016.01) |
| *C08K 3/22* | (2006.01) |
| *C08K 5/053* | (2006.01) |
| *C08K 3/30* | (2006.01) |
| *A61L 31/04* | (2006.01) |
| *C08K 3/06* | (2006.01) |
| *C08K 5/07* | (2006.01) |
| *A61B 17/00* | (2006.01) |

(52) U.S. Cl.
CPC .............. *C08J 5/02* (2013.01); *A61B 42/10* (2016.02); *A61L 31/049* (2013.01); *C08K 3/06* (2013.01); *C08K 3/22* (2013.01); *C08K 3/30* (2013.01); *C08K 5/053* (2013.01); *C08K 5/07* (2013.01); *A61B 2017/00526* (2013.01); *C08J 2309/04* (2013.01); *C08K 2003/222* (2013.01); *C08K 2003/2227* (2013.01); *C08K 2003/2241* (2013.01); *C08K 2003/2296* (2013.01); *C08K 2201/014* (2013.01); *C08K 2201/019* (2013.01)

(58) Field of Classification Search
CPC .................. A61B 42/10; C08K 3/105
See application file for complete search history.

(56) References Cited

U.S. PATENT DOCUMENTS

| 2,662,874 A | 12/1953 | Brown |
| 2,859,193 A | 11/1958 | Kowalewski |
| 2,868,754 A * | 1/1959 | Eilbeck et al. ......... C08F 36/04 |
| | | 524/821 |
| 3,403,136 A | 9/1968 | Baker |
| 3,976,723 A | 8/1976 | Williams et al. |
| 4,525,517 A | 6/1985 | Sato |
| 5,014,362 A | 5/1991 | Tillotson et al. |
| 6,000,061 A | 12/1999 | Taneja et al. |
| 6,492,446 B1 | 12/2002 | Kajiwara et al. |
| 6,828,387 B2 | 12/2004 | Wang et al. |
| 7,721,354 B2 | 5/2010 | Yu et al. |
| 8,273,810 B2 | 9/2012 | Wang et al. |
| 9,085,100 B2 | 7/2015 | Foo |
| 2004/0030027 A1* | 2/2004 | Konno ............ C08K 3/22 |
| | | 524/493 |
| 2008/0139723 A1 | 6/2008 | Foo |
| 2008/0227913 A1 | 9/2008 | Koide |
| 2012/0204321 A1 | 8/2012 | Connelly et al. |
| 2017/0099889 A1* | 4/2017 | Liou ............ C08F 236/12 |
| 2017/0137584 A1* | 5/2017 | Tung ............ C08K 3/10 |

FOREIGN PATENT DOCUMENTS

| EP | 1209186 A1 | 5/2002 |
| GB | 851045 A | 10/1960 |
| GB | 862372 A | 3/1961 |
| WO | 2004044037 A1 | 5/2004 |
| WO | 2009134702 A1 | 11/2009 |
| WO | 2015/006606 A1 | 1/2015 |
| WO | 2015006807 A1 | 1/2015 |
| WO | 2015006808 A1 | 1/2015 |
| WO | WO 2015/006808 * | 1/2015 |
| WO | 2016/072635 A1 | 5/2016 |

(Continued)

OTHER PUBLICATIONS

"Alkali" Van Nostrand's Encyclopedia of Chemistry, Copyright © 2005 (Year: 2005).*
"Alkali" Hawley's Condensed Chemical Dictionary, R. J. Lewis (Ed.), 2007 (Year: 2007).*
Datta, R.N., "Rubber Curing Systems", Rapra Review Reports, Report 144, vol. 12, No. 12(2002) (in English; 157 pages).
Joseph, Rani, "Practical Guide to Latex Technology", Smithers Rapra Technology, Ltd. (2013) (in English; 121 pages).
<Klingender, Robert C., "Handbook of Specialty Elastomers", published by CRC Press, Taylor & Francis Group, (2008) (in English; 572 pages).

(Continued)

Primary Examiner — Robert C Boyle
(74) Attorney, Agent, or Firm — Westerman, Hattori, Daniels & Adrian, LLP

(57) ABSTRACT

This application relates to synthetic elastomeric articles, such as gloves, comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0. Also described are compositions for forming the articles, and methods for making the articles, based on the use of the described cross-linking composition. The articles, compositions and methods contain a second cross-linking agent comprising either (a) sulphur and a sulphur donor, (b) a multivalent metal oxide or ionic cross-linking agent, (c) sulphur, a sulphur donor and an ionic cross-linking agent, or (d) sulphur donor.

29 Claims, 5 Drawing Sheets

(56) References Cited

FOREIGN PATENT DOCUMENTS

WO      2016072835 A1     5/2016
WO      2017/116227 A1    7/2017

OTHER PUBLICATIONS

Extended European Search Report, dated Sep. 16, 2019, issued in counterpart European Application No. 16886828.9 (in English; 7 pages).

* cited by examiner

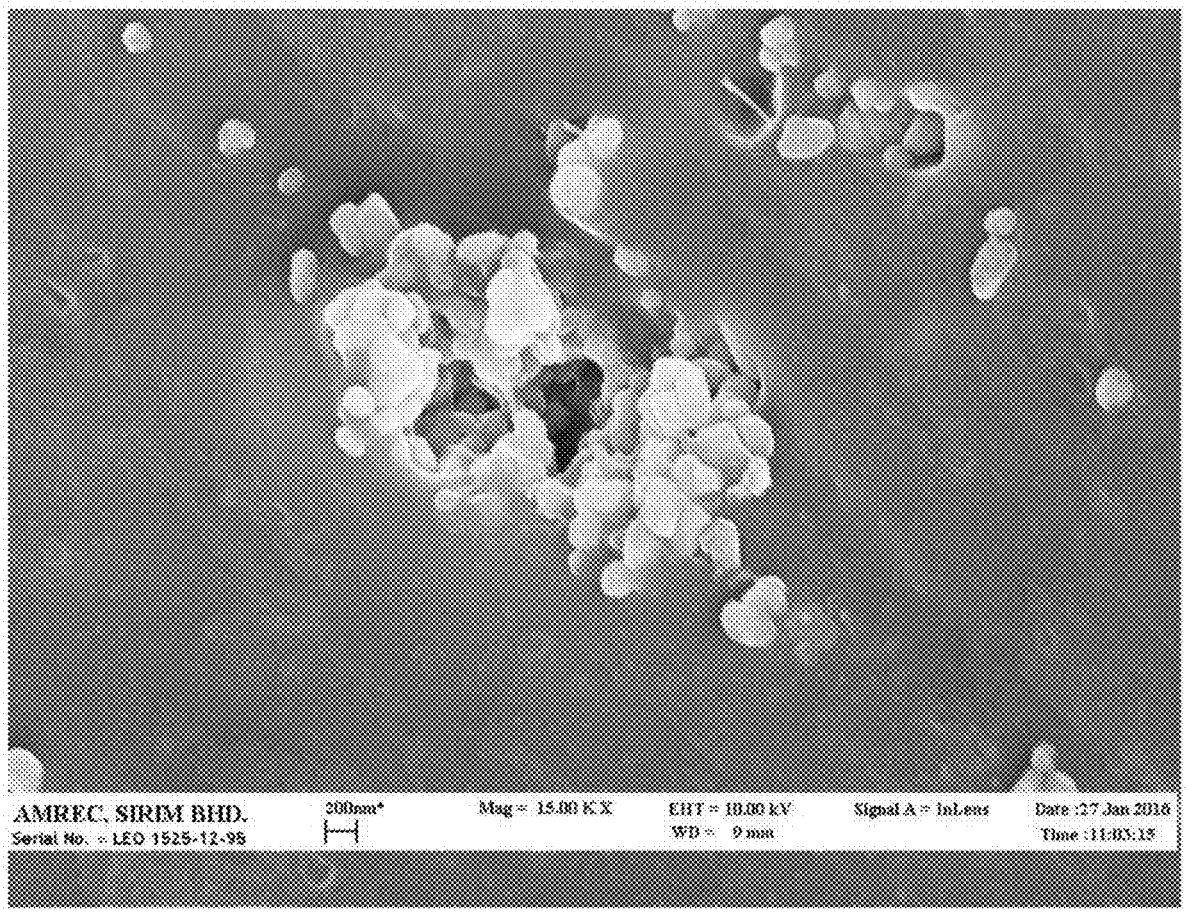
Figure 1 (9-2) : The cluster of white particles is TiO2 particles

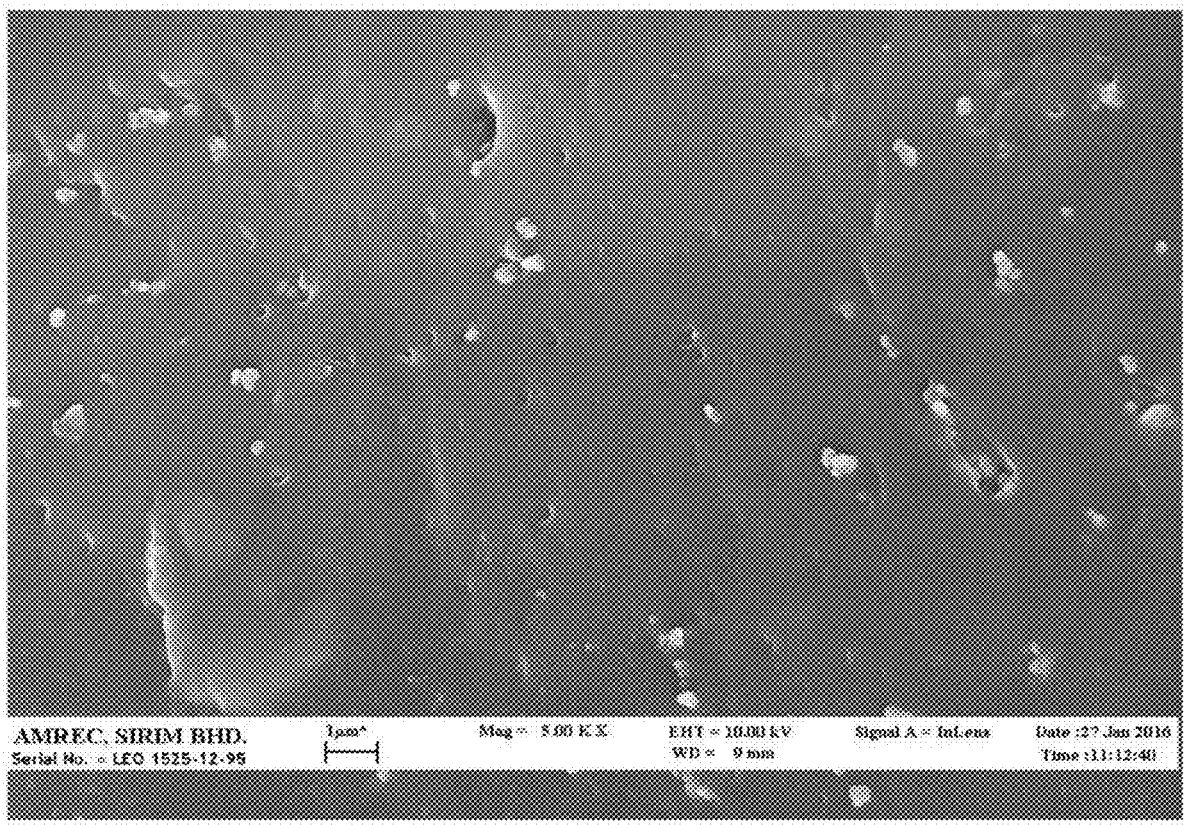
Figure 2 (9-2): The cluster of white particles is TiO2 particles

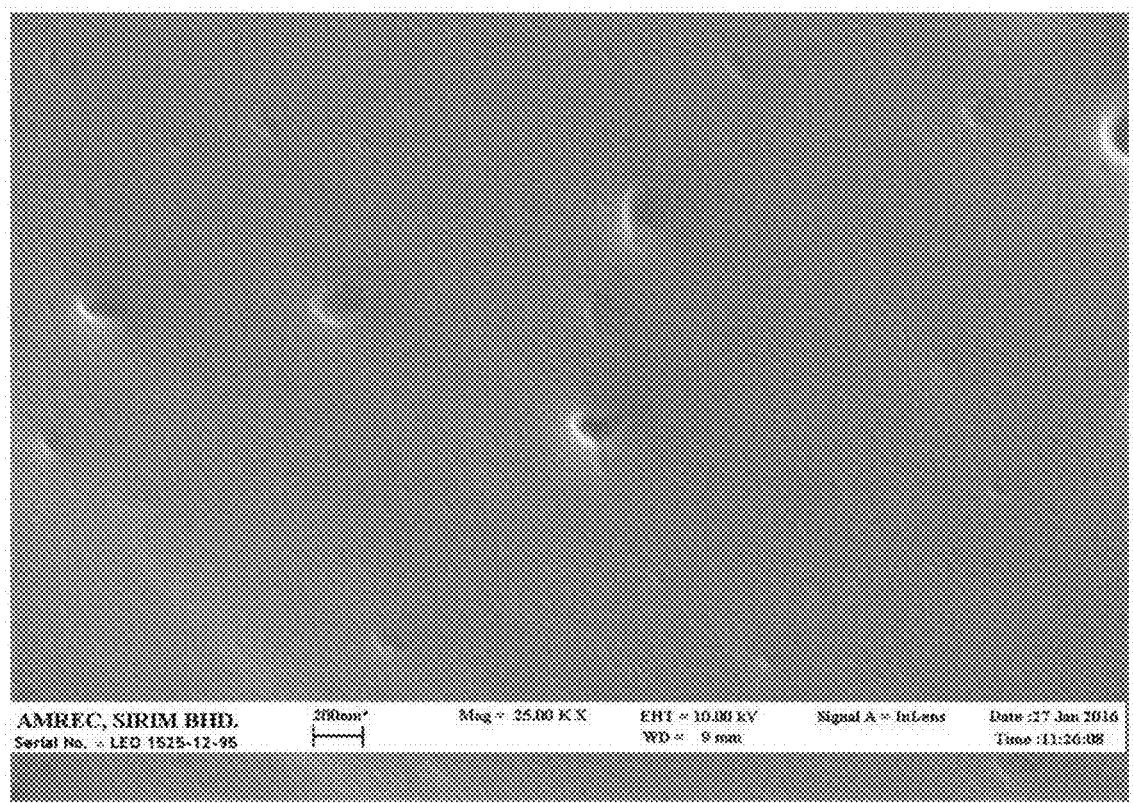
Figure 3 (9-1) – 25000x : The above uniform surface shows the proper and even distribution of Al inside the elastomeric matrix (the visible dents are surface untulations)

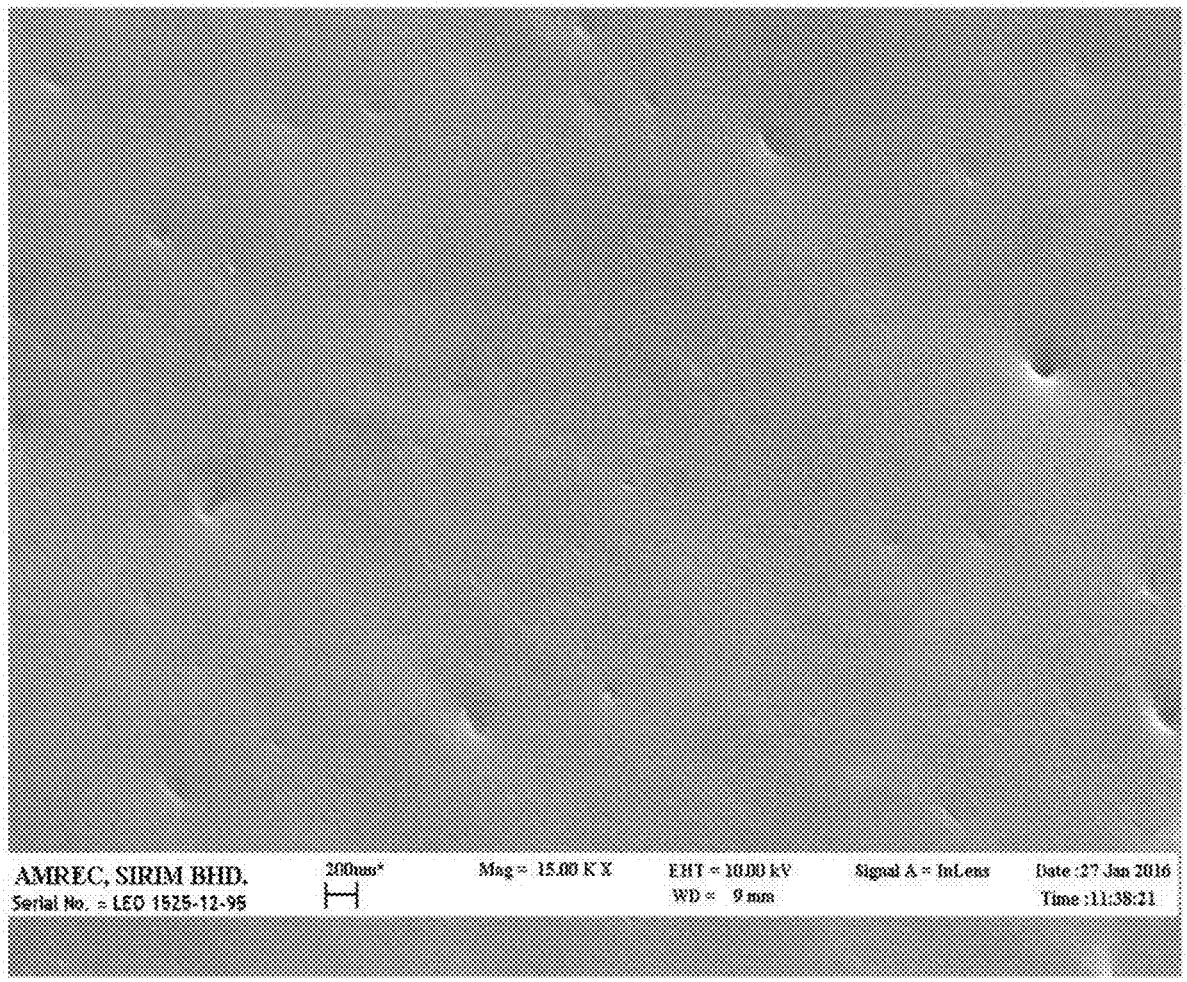
Figure 4 (9-1) 15000x: The above uniform surface shows the proper and even distribution of Al inside the elastomeric matrix (the visible dents are surface untulations)

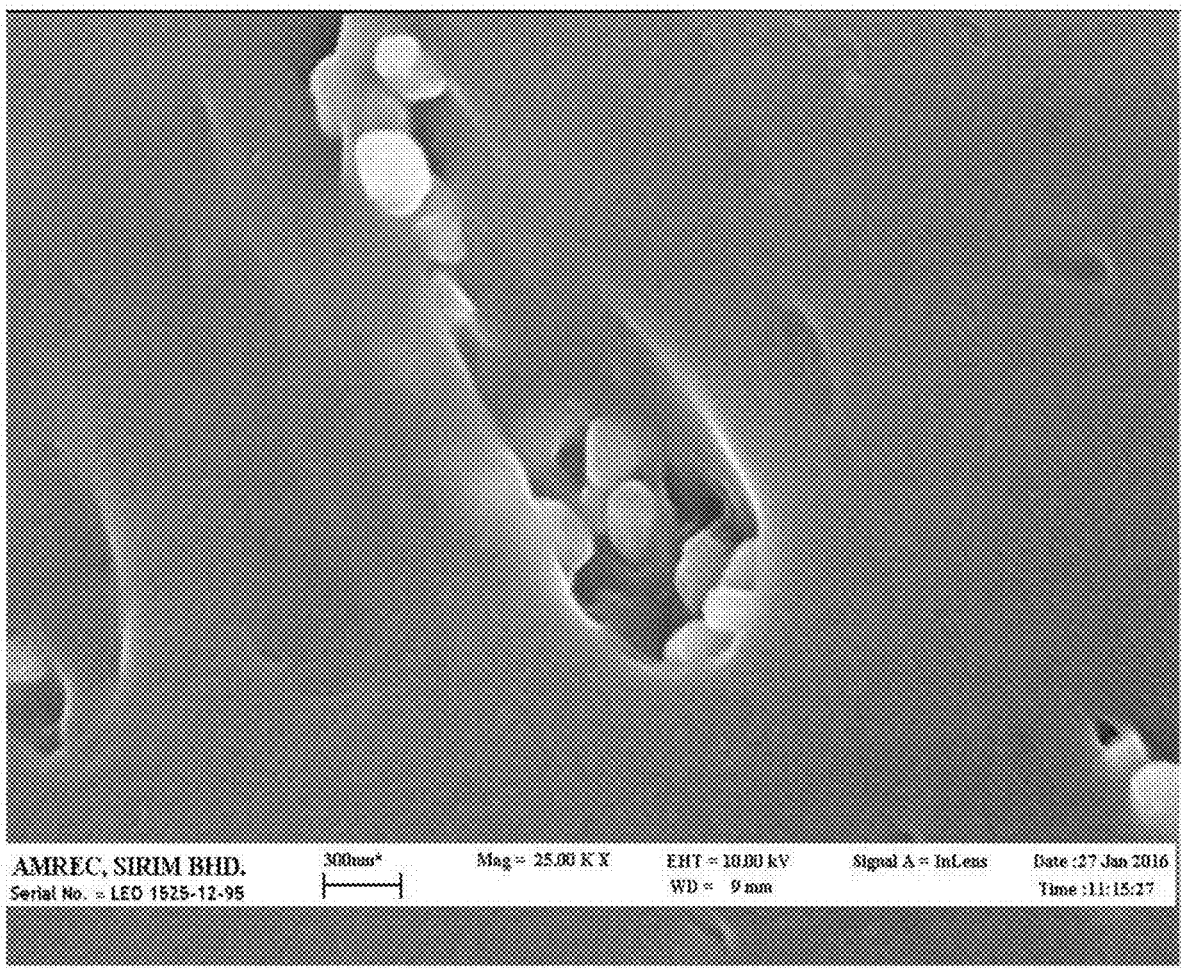
Figure 5 (9-2): The cluster of white particles is TiO2 particles

ELASTOMERIC ARTICLES, COMPOSITIONS, AND METHODS FOR THEIR PRODUCTION

FIELD

The present invention relates to elastomeric articles, compositions, and methods for their production. The articles may be in the form of films, gloves, condoms or otherwise. The compositions are suitable for forming articles through a dipping processes.

BACKGROUND

Important properties in the formation of many elastomeric articles are elasticity, the maintenance of elastic properties on stretching, and softness. In the case of elastomeric gloves, and particularly thin film gloves, these properties are very important and impact on the comfort of the gloves to persons wearing them.

When a thin film glove is worn for barrier protection by a person, the gloves can become uncomfortable after a short period of time, due to fatigue associated with the resistance of the glove, which is in turn a result of an intrinsic character known as "lesser elasticity". This property is measured in terms of its modulus (which may be measured at 500%, or preferably at 300%). It is desirable for a glove for use in such applications to have a lower modulus.

In relation to elasticity, it is often desirable in certain applications for the elastomeric article to have high elasticity properties, as indicated by a high capacity to be stretched, or elongated, before breakage. This is measured by a test that determines elongation, or more specifically, elongation at break.

It is difficult to achieve a balance of a low modulus, combined with high elongation at break, as well as desirable "feel" or touch properties, particularly without the additional potential problems that may arise through the incorporation of potential allergens. Gloves that are made from natural (polyisoprene) rubber have favourable feel and comfort properties, and can be made with a good balance between favourable modulus and elongation properties. However, natural (polyisoprene) rubber is associated with a potential allergen that causes Type I allergy. Accordingly, articles formed from synthetic elastomer alternatives having the same or improved properties compared to natural rubber are desired.

The current trend is to use nitrile rubber, (synthetic) polyisoprene rubber, polychloroprene rubber, styrene butadiene rubber, butyl rubber and/or vinyl in the production of elastomeric articles, such as gloves. These polymers are traditionally cross-linked with finely milled (solid) zinc oxide and/or sulphur cross-linking agents. Some of these materials do not provide the favourable feel and comfort of natural polyisoprene rubber. Others of the known cross-linked synthetic polymers, while having reasonable feel and comfort properties, are very expensive, making them unsuitable for the production of low cost, disposable elastomeric articles, such as gloves, condoms and the like. Although reducing the thickness (weight) of such articles made from the more expensive elastomeric polymers has been considered, reduced thickness products are at an increased risk of containing defects. The defects may be in the form of holes due to poor film formation at such fine thicknesses and/or lower endurance properties compared to the properties required by the consumer.

Elastomeric compositions have potential application in many fields, and can be used in the production of elastomeric articles other than thin film gloves (including medical gloves, surgical gloves, examination gloves) and condoms. Other examples of elastomeric articles include those for medical applications such as catheters, tubing, protective coverings, balloons for catheters and the like, and those for use in non-medical applications, such as industrial gloves, laboratory gloves, household gloves, gardening gloves, electrical gloves, irradiation gloves, finger cots, weather balloons, clean room gloves for electronic industries, gloves for food contact and food processing and biotechnical application and the like. By expanding the range of potential new elastomeric film compositions that are available, particularly low cost elastomeric article compositions, the compositions can be used in the production of a wider range of these articles, and new applications for the compositions may be developed.

In some applications and embodiments, it may also be desirable to provide new elastomeric articles, formed from new compositions, that can be produced at reduced cost. The areas for potential cost reduction may be the cost of the input components or reagents, the physical processing costs (including energy costs for performing certain production steps), and so forth.

In some applications and embodiments it may be desirable to avoid the use of reagents that have, or may have, an adverse impact on the environment.

It is an object of the present invention to provide new elastomeric articles, and compositions for the production of such articles, that provide one or more of the desired features described above.

SUMMARY

According to the present invention, there is provided a synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0.

According to the present invention, there is also provided an elastomeric article-forming composition (also referred to as a "synthetic latex composition" or "latex composition" for short) comprising:
  a synthetic carboxylated polymer, and
  a cross-linking composition, the cross-linking composition comprising an aqueous solution of a negatively-charged multivalent metal complex ion having a pH of at least 9.0.

According to the present invention there is also provided a method of manufacturing a synthetic elastomeric article comprising:
  adding a cross-linking composition comprising an aqueous solution of a negatively-charged multivalent metal complex ion having a pH of at least 9.0 to an aqueous suspension of a synthetic carboxylated polymer having a pH of at least 9.0 to produce a synthetic latex composition;
  forming the synthetic latex composition into the shape of the synthetic elastomeric article; and
  curing the synthetic latex composition to form the synthetic elastomeric article.

In contrast to prior art articles and compositions, the articles and compositions of the present invention involve the use of a solubilised form of a multivalent metal, in a complex ion form which has an overall negative charge, at a pH of at least 9.0. The multivalent metal then forms cross-links between carboxyl groups of the carboxylated polymer during the cross-linking or curing stage in the manufacture of the article. Through the exercise of considerable skill and effort, the inventors were able to achieve solubilisation of the multivalent metal and maintenance of the multivalent metal in solution without (or without significant) precipitation of insoluble forms of the multivalent metal during the time of adding the cross-linking agent to the suspension of synthetic carboxylated polymer in water. Combining of the cross-linking agent with the aqueous suspension of synthetic carboxylated polymer was conducted very carefully to avoid disruption to the suspension of the polymer in water—that is, without disruption of the emulsion. One key factor in enabling this to be achieved involves controlling the pH of the respective cross-linking composition and the aqueous suspension of the synthetic carboxylated polymer. Other factors that assist in achieving this result are set out in the detailed description below.

In key embodiments of the present invention, the synthetic latex composition further comprises a second cross-linking agent comprising either (a) sulphur and a sulphur donor, (b) a multivalent metal oxide or ionic cross-linking agent, (c) sulphur, a sulphur donor and an ionic cross-linking agent, or (d) sulphur donor.

Thus, in one aspect, there is provided a synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0, the synthetic latex composition further comprising a second cross-linking agent comprising either (a) sulphur and a sulphur donor, (b) a multivalent metal oxide or ionic cross-linking agent, (c) sulphur, a sulphur donor and an ionic cross-linking agent, or (d) sulphur donor.

In another aspect there is provided an elastomeric article-forming composition comprising:
  a synthetic carboxylated polymer,
  a cross-linking composition, the cross-linking composition comprising an aqueous solution of a negatively-charged multivalent metal complex ion having a pH of at least 9.0, and
  a second cross-linking agent comprising either (a) sulphur and a sulphur donor, (b) a multivalent metal oxide or ionic cross-linking agent, (c) sulphur, a sulphur donor and an ionic cross-linking agent, or (d) sulphur donor.

In a further aspect there is provided a method of manufacturing a synthetic elastomeric article comprising:
  adding (i) a cross-linking composition comprising an aqueous solution of a negatively-charged multivalent metal complex ion having a pH of at least 9.0 and (ii) a second cross-linking agent comprising either: (a) sulphur and a sulphur donor, (b) a multivalent metal oxide or ionic cross-linking agent, (c) sulphur, a sulphur donor and an ionic cross-linking agent, or (d) sulphur donor, to an aqueous suspension of a synthetic carboxylated polymer having a pH of at least 9.0 to produce a synthetic latex composition;
  forming the synthetic latex composition into the shape of the synthetic elastomeric article; and
  curing the synthetic latex composition to form the synthetic elastomeric article.

The use of these selected second cross-linking agent combinations (or sole secondary agents) provides for particularly good properties in combination with the negatively-charged multivalent metal complex ions of the primary cross-linking composition. The use of these agents in combination with the multivalent metal ions allows for low reagent utilisation in the production of gloves, and also produces gloves having excellent properties, as demonstrated in various examples in this specification.

The synthetic carboxylated polymer typically comprises synthetic carboxylated polymer particles. Reaction of the solubilised multivalent metal with the carboxylated polymer particles is understood to result in a cured product in which the synthetic carboxylated polymer particles are bonded to each other through intra-polymer particle multivalent metal cross-links and inter-polymer particle multivalent metal cross-links, in which the intra-polymer particle and inter-polymer particle multivalent metal cross-links are uniformly distributed throughout the cured product.

Thus, according to a further embodiment of the invention, there is provided a synthetic elastomeric article comprising cured synthetic carboxylated polymer particles bonded to each other through intra-polymer particle multivalent metal cross-links and inter-polymer particle multivalent metal cross-links, in which the intra-polymer particle and inter-polymer particle multivalent metal cross-links are uniformly distributed throughout the cured product.

According to another embodiment of the invention, there is provided a cross-linking composition comprising an aqueous solution of a negatively-charged multivalent metal complex ion having a pH of at least 9.0. According to preferred embodiments, this cross-linking composition further comprises a mechanical stabiliser and/or a surfactant.

DETAILED DESCRIPTION

The synthetic elastomeric article, composition and methods of manufacture are described in further detail in this section.

Cross-Linking Composition

The present inventors have developed a new form of cross-linking agent composition, which is based on an aqueous solution of a negatively-charged multivalent metal complex ion having a pH of at least 9.0.

The inventors developed this invention using the example of sodium aluminate in the production of negatively-charged multivalent metal complex ions, in which the multivalent metal is aluminium. However, as described in detail below, embodiments of the invention are applicable to a wider range of multivalent metals, and sources of the metals, in the production of the cross-linking composition. In this introductory portion of the detailed description, reference is made to the example of negatively-charged aluminium complex ions, and sodium aluminate as a source for those ions, to illustrate the invention and explain the advantages that are obtained over prior art compositions. However, this should be read in this context and should not be understood as confining the scope of the invention.

In the prior art, it is common to use zinc oxide as an ionic cross-linking agent in the production of elastomeric articles such as gloves. Zinc oxide, and other oxides of the multivalent metals, are typically insoluble in water. Zinc oxide is incorporated into latex compositions used in the formation of elastomeric gloves in solid form. Zinc oxide does not have significant solubility in water. In high pH environments, there may be some diffusion of the solid zinc oxide into solution, but this process is slow and incomplete. The zinc oxide is typically finely milled, to provide a high surface area to the reagent to maximise availability of the zinc oxide to produce ionic zinc cross-links with the polymer being cross-linked, to form a cross-linked or cured product. The milling step requires energy input to achieve. In addition, there is incomplete usage of the zinc, and thus the amount added (measured in terms of phr—"per hundred parts rubber") must be high enough to allow for the incomplete reaction of the reagent. Zinc also finds its way into the air or wastewater during manufacturing, use or recycling of products containing zinc. This can have an adverse environmental impact, and it is becoming more important to reduce or remove zinc from products.

Another problem with conventional zinc oxide is associated with the manner in which solid zinc oxide forms cross-links within the final product. As explained above, the synthetic carboxylated polymer is in the form of a particulate suspension or emulsion in water. When using solid zinc oxide as the cross-linking agent, the cross-links tend to be concentrated around the particles, and the cross-links are predominantly inter-particle cross links. In this regard, reference is made to WO09/134702, which includes spectral information showing the typical pattern of zinc in the product when solid zinc oxide is used as an ionic cross-linking agent. The zinc is concentrated around the particles, and decorates the particles. Soluble forms of sulphur in that case are allowed to penetrate into the particles, and form inter-particle cross-links. There is little penetration of the zinc into the polymer particles, if any, in view of the lack of any significant solubility of zinc in typical latex emulsions under typical conditions.

In the art of the invention, it is uncommon in practice to modify products to use ionic cross-linking agents other than the well-known and well understood zinc oxide, and other solid multivalent metal oxides. Even if they had been considered from a theoretical perspective, it is the present inventors' experience that it is extremely difficult in practice to put this idea into effect.

Nevertheless, after considerable effort, the present inventors were able to produce a solubilised form of multivalent metal cross-linking agent, and were able to combine this with an aqueous suspension of synthetic carboxylated polymer, and were able to produce a synthetic latex composition that is very effective in creating elastomeric articles having excellent properties. The inventors found that it is not sufficient to add a solid form of the multivalent metal (such as zinc oxide) to the synthetic latex composition, and to seek to increase the pH and take additional steps to attempt to solubilise the multivalent metal. As an example, taking solid zinc oxide or another solid oxide and adding this to an aqueous suspension of synthetic polymer (carboxylate or otherwise) and then attempting to solubilise the oxide in situ through pH adjustment or heating is not effective. Instead, a stable aqueous solution of negatively charged multivalent metal complex ions must be prepared as a preliminary step, with optional stabiliser and/or surfactant addition, and with pH control, and this composition is to be added in a controlled manner to the aqueous suspension of synthetic polymer which is also subjected to pH control. The streams are then to be carefully combined while avoiding disruption of the emulsion, latex lump formation through micro-coagulation, precipitation or other settling of the components from the composition.

In some embodiments it is additionally important to control other factors in the composition, article or process. The features of such embodiments are described in further detail below.

Multivalent Metal

The term "multivalent metal" refers to a metal having a valency of two or more. The expression "divalent or higher valency" may be used interchangeably with "multivalent". In some embodiments, the multivalent metal is a trivalent metal.

Whilst aluminium is the preferred multivalent metal, in some embodiments, the multivalent metal of the negatively-charged multivalent metal complex ion can be another of the class of amphoteric metals. The amphoteric metals are those metals that form amphoteric substances from their oxides and/or hydroxides. This class includes aluminium, beryllium, chromium, zinc, copper, iron, cobalt, lead, tin, bismuth, gallium, indium, scandium, titanium, zirconium, vanadium, silver, gold, germanium, antimony and tellurium. The multivalent metal of the negatively-charged multivalent metal complex ion is preferably selected from the group consisting of aluminium, beryllium, chromium, iron, cobalt, copper, zinc, lead, tin and bismuth. The multivalent metal may be selected from aluminium and beryllium. Trivalent (or higher valency) metals are preferred, and aluminium is most preferred in selected embodiments.

To produce the cross-linking composition, initially a solution is formed by dissolving a source of the multivalent metal in water. This may be achieved with heating and the optional addition of an alkali and/or a mechanical stabiliser and/or a surfactant. In some notable embodiments, it is a feature that a mechanical stabiliser and/or surfactant is included in the cross-linking composition.

Regarding the source of the multivalent metal, a suitable source needs to be chosen that is capable of yielding a solution of negatively charged multivalent metal complex ions. This may require pH adjustment of the solution to achieve solubilisation. Suitable sources included (a) a multimetal oxide of the multivalent metal, (b) a hydroxide of the multivalent metal or (c) a salt of the multivalent metal.

Regarding the first class, being the multimetal oxides of the multivalent metal, this term refers to an oxide of the multivalent metal with another one or more different metal species. Such multimetal oxides of the multivalent metal may be referred to as "multimetal oxides" in short. Such materials may also be viewed as a mixed metal oxides. Where there are two metals, the oxide may be described as a double metal oxide. The second metal species may be, for example, an alkali metal, such as sodium or potassium. In the case of aluminium as the multivalent metal, the second metal species is preferably sodium or potassium, also referred to as sodium aluminate and potassium aluminate. Thus, in one example, the multimetal oxide of the multivalent metal may be an alkali metal-multivalent metal oxide.

Regarding the second class, being hydroxides of the multivalent metal, these may simply be referred to as metal hydroxides. In practice, to achieve the production of the negatively charged multivalent metal complex ion, a second hydroxide (such as an alkali metal hydroxide) is required, with a consequent increase in the pH required for solubilisation of the multivalent metal hydroxide. The hydroxides of the multivalent metals may in some cases be viewed as the hydrated multivalent metal oxides, and the source of the multivalent metal hydroxide may in practice be a multivalent metal oxide (particularly a mixed metal oxide). In solution, there may be a mixture of different hydroxides of the multivalent metal, in different complex ion forms. This is elaborated on in further detail below using the example of aluminium.

Regarding the third class, being the salts of the multivalent metals, the salt will typically require considerable alkali addition (such as alkali metal hydroxide) to achieve solubilisation of the multivalent metal and production of the negatively charged multivalent metal complex ions. Solutions of multivalent metal salts are not typically alkaline, and it may be necessary to add considerable alkali to raise the pH to at least 9.0. It is important in such cases for the negatively charged multivalent metal complex ions to be produced on raising the pH, without significant precipitation of an insoluble salt. Examples of salts include alum (potassium alum, or potassium aluminium sulphate), poly aluminium chloride (also referred to as $AlCl_3$), and poly ferric sulphate. The pH of 10% solutions of these salts are 2.83, 3.27 and 1.7, respectively, so considerable alkali (in the form of alkali hydroxide) is required to raise the pH to at least 9.0 and to form the negatively charged multivalent metal complex ions.

The first two classes are preferred, thus it is preferred that the cross-linking composition comprises a solution of a multimetal oxide of the multivalent metal or a solution of a multivalent metal hydroxide.

Of the range of multivalent metals, the source of multivalent metal may only be available from one or two of the above groups of potential sources ((a), (b) and (c)). Thus, in the case of iron, iron hydroxide is not a suitable source for the preparation of solubilised negatively charged iron complex ions due to its lack of solubility. In the case of aluminium as the multivalent metal, sources from each of the possible groups ((a), (b) and (c)) are available.

As indicated above, in some embodiments, the cross-linking composition comprises a solution of sodium aluminate, producing negatively-charged aluminium complex ions. The primary ions formed are the tetrahydroxoaluminate (III) ions—being a complex of a central aluminium atom with co-ordinating hydroxo ligands. Aqua (water) ligands may also form part of the complex ions. Other ions in the solution will include the aluminium and alkali metal (e.g. Na). The range of negatively charged aluminium complex ions produced on solubilising sodium aluminate is reported in the literature. At varying pH levels, the equilibrium between the various ions will differ. The key to maintaining soluble aluminium complex ions is to maintain the pH above 9.0, as below 9.0 insoluble $Al(OH)_3$ is formed, which precipitates out of solution. With other multivalent metals, the pH must be such that the soluble negatively-charged complex ions of the multivalent metal are formed, and an insoluble precipitate is minimised or avoided. In this regard, preferably not more than 20%, more preferably not more than 15%, 10%, 5% or less than 2% of the multivalent metal is in the form of an insoluble precipitate (precipitated out of solution). These percentages apply regardless of the source used, and regardless of the identity of the multivalent metal that is solubilised to form the negatively-charged multivalent metal complex ion.

Sodium aluminate is a basic inorganic chemical used in water and effluent treatment industries. These salts are used as coagulants to settle fine particulate materials in water streams, such as bicarbonates. This is available at low cost, which allows for reduced cost of production of the new elastomeric articles of the present invention, which may lead to the development of new applications for the elastomers. Being a water treatment chemical, sodium aluminate is also considered to be safe for use, and safe for food-contact applications.

Other advantages associated with the use of sodium aluminate, or other cross-linking agent sources as described herein, are as follows:

There is no cost associated with milling (in contrast to solid zinc oxide and other prior art solid cross-linking agents)

It is possible to eliminate zinc usage, if so desired. In such embodiments, the cross-linking composition is free of zinc, or substantially free of zinc. In some embodiments, the latex composition is also free of zinc, or substantially free of zinc. Eliminating zinc will avoid excess liberation of zinc to the environment. In some countries such as Japan, there are limits on the detectable level of zinc in components involved in food handling. (Note that it is nevertheless an option in some embodiments to use a second cross-linker which is based on a different multivalent metal oxide compared to the solubilised one, such as zinc oxide, as described in further detail below.)

Aluminium has a low atomic weight of 27 and a specific gravity of 2.7. Compared to conventional cross-linkers, such as zinc (atomic weight 65 and specific gravity 7.14) this is low. Per molecule that requires cross-linking, less weight of aluminium-based reagent is required. This allows for further cost reduction in the manufacture of elastomeric articles using aluminium (or similar) ionic cross-linking agent, particularly when little or no zinc cross-linking agent is added.

Aluminium has a valency of 3, allowing for 3-links per molecule. In contrast, zinc, with a valency of 2, allows for 2-links per molecule. This allows for a theoretical 50% in the cross-linking ability of aluminium compared to zinc, even leaving aside the solubilising effect (compared to solid zinc oxide). This is another factor that allows for reduction in the mass of ionic cross-linking agent to be used.

Aluminium in this form is not subject to purity concerns, allowing it to be used in a range of applications. Aluminium is abundant, and safe for food applications (as reflected by the use of aluminium foil food packaging.)

In view of the effectiveness of the cross-linking with the solubilised multivalent metal, it is possible to produce products with lower, or no, sulphur, and/or lower, or no, sulphur donor materials. This also applies to embodiments using multivalent metals other than just aluminium. Whilst it is possible to produce products with lower, or no, sulphur and/or lower, or no, sulphur donors, in some embodiments, excellent products can be produced containing either (a) sulphur and a sulphur donor, (b) a multivalent metal oxide or ionic cross-linking agent, (c) sulphur, a sulphur donor and an ionic cross-linking agent, or (d) sulphur donor, as the second cross-linking agent. In such embodiments it is possible to produce excellent products suitable for commercial production containing low levels of the solubilised multivalent metal oxide, hydroxide or salt, with low levels of the sulphur and sulphur donor (alone or with an ionic cross-linking agent), or sulphur donor alone.

If the option is taken to form the product without sulphur and sulphur donor materials, which is possible in view of the cross-linking performance of the composition (particularly when a second cross-linking agent that is an organic cross-linking agent other than sulphur or a sulphur donor is used), the product is free of Type IV allergens. Further, as natural rubber is not used (containing proteins and other potential Type I allergens), the products are also free of type I allergens. This also applies to embodiments using multivalent metals other than just aluminium.

Homogeneity is improved, as a consequence of lightness and the ionic nature of the negatively-charged complex. Intra-particle cross-links can be formed at a similar distribution to the inter-particle cross-links. Homogeneity can be further maximised through the use of stabilising agents, as described below. This also applies to embodiments using multivalent metals other than just aluminium.

Loss due to milling wastage is avoided. Loss due to settling during storage or in the dipping tank is avoided. This also applies to embodiments using multivalent metals other than just aluminium, since in each case a solubilised form of multivalent metal is used.

The multivalent metal, in aqueous ionic form, can instantly react with the carboxylic groups on the polymer. This can be achieved at room temperature, thus leading to potential cost savings associated with avoided heating. Whilst the cross-linking can be conducted at lower temperature (e.g. <40° C. or <30° C.), higher temperatures may still be used to achieve cross-linking of second cross-linking agent(s), if present. This also applies to embodiments using multivalent metals other than just aluminium.

Dipped articles produced using the cross-linking composition have high tensile value at break (greater than 1000 psi (6.9 MPa), or even up to 6000 psi) and elongation to break (greater than 400%, typically greater than 650%, or greater than 700%, or as high as 900% or more). Lower modulus at 300% and at 500% are also obtained. Modulus values at 500% (aged and unaged) can be so low as to be below 7.0 MPa, or below 6.9, 6.8, 6.7, 6.6, 6.5, 6.4, 6.3, 6.2, 6.1, 6.0 or even lower. This applies in particular to films having a thickness of less than 2.0 mm (i.e. an average thickness across three test points, for a sample size of at least 10 articles). This also applies to even thinner films (less than 1.9 mm, less than 1.8 mm films, etc). The examples demonstrate that the physical properties are directly proportional to the ppm level of multivalent metal (corresponding to the amount of multi metal oxide source used in forming the cross-linking composition). This also applies to embodiments using multivalent metals other than just aluminium, although aluminium-based cross-linking agents give particularly good results. Further, and surprisingly, embodiments using low levels of aluminium-based solubilised cross-linking agents provide particularly good results with low input of total cross-linking agents (in phr).

Articles, such as gloves, made using the cross-linking composition and through the associated method have been found to possess highly favourable characteristics such as favourable feel and comfort, and improved softness. The gloves have high elasticity, as indicated by a high % elongation at break, and/or a very low modulus at 500% —both aged and unaged, even with low thickness levels (average 2.0 mm or less). Gloves can be made from very thin layers of elastomeric film without increasing the presence of defects such as pin holes, weak spots or other defects. These improvements may be even better when using the combination of one or more surfactants, additional cross-linking agents, and optionally a second polymer which is a carboxylated or non-carboxylated synthetic polymer. This also applies to embodiments using multivalent metals other than just aluminium.

Gloves made from the product are easy to don. This also applies to embodiments using multivalent metals other than just aluminium.

Alkali in Cross-Linking Composition and pH

In embodiments of the invention, the cross-linking composition further comprises alkali. This may be added in the form of sodium hydroxide, potassium hydroxide or ammonium hydroxide. Sodium and/or potassium hydroxide are most typically used. The alkali serves to increase the pH to the level required for solubilisation and/or to chemically stabilise the solution of negatively charged multivalent metal complex ions.

In some embodiments, a combination of sodium hydroxide and potassium hydroxide is used. The sodium hydroxide interacts with the aluminium (where this is the multivalent metal) in the formation of complex ions. Potassium hydroxide is more commonly used in latex compositions, and the presence of potassium hydroxide as one of the alkalis assists in avoiding potential localised coagulation when the cross-linking agent is added to the aqueous suspension of synthetic carboxylated polymer. If sodium hydroxide alone is used as the alkali, there is a risk of localised coagulation when the cross-linking agent is added to the aqueous suspension of the polymer, due to the high activation energy of sodium ions. The relative amount of sodium hydroxide to potassium hydroxide may be about 3:1 to 1:3. The amount may be about 2:1 (sodium to potassium) or about 1:1.

The pH of the cross-linking composition is important. The pH must be such that solubilisation of the multivalent metal is achieved, through production of negatively charged multivalent metal complex ions. It is also a feature of the method of embodiments of the invention that the pH of the cross-linking composition is "matched" to the pH of the aqueous suspension of synthetic carboxylated polymer. This is described in further detail below. In general terms, the pH should be high enough to achieve solubilisation of the multivalent metal. This may be between 9.0 and 13.5, such as between 9.0 and 13.0, 9.0 and 12.5, 9.0 and 12, between 9.0 and 11.5, such as between 9.0 and 11.0, 9.2 and 11.0, 9.5 and 11.0, 9.5 and 10.5, 9.8 and 10.8, 10.0 and 11.0, or 10.0 and 10.8. When a salt form of the multivalent metal is used, it is preferred to use a higher pH to subdue the acidic properties, so a pH of around 10.0-13.0 may be desired, such as between about 11.5 and 12.5, or about 12.

In addition to influencing the pH of the cross-linking composition, the alkali has an influence on the stability of the complex ions in solution. Sodium from sodium hydroxide stabilises the complex ions in solution. Higher amounts of sodium hydroxide allow for greater activation of the multivalent metal (e.g. aluminium) in the complex, and allows for a reduced amount of multivalent metal source to be used in the composition.

Mechanical Stabiliser in the Cross-Linking Composition

While it is possible for the cross-linking composition to be prepared without any mechanical stabiliser, it is advantageous to include in the cross-linking composition a mechanical stabiliser for mechanically (i.e. structurally) maintaining the negatively-charged multivalent metal complex ions in solution. The mechanical stabiliser aids on maintaining the stability of the solution, by providing structural support around the complex ions to avoid re-precipitation or re-crystallisation. The mechanical stabiliser may be any agent that has this function. The mechanical stabiliser may be a water-miscible or water-soluble organic polyol, or a water-soluble or water-miscible thickening agent, examples of which are well known in food or pharmaceutical manufacture. Examples of such polyols and thickeners include glycerine, sugars and sugar alcohols, maltodextrin, polysaccharide, polyglycerol, polyethylene glycols, starch, modified starch, and mixtures thereof.

Amounts of Components in the Cross-Linking Composition

The amount of multivalent metal in the latex composition may be anywhere between 0.01-5 phr across the range of embodiments described herein. Although that is the case, in particular embodiments, the phr amounts used may fall within a narrower range of values. Amounts in "phr" are commonly used in the art. Phr refers to parts per hundred parts of rubber (i.e. per hundred parts of the polymer), by weight. In cases where reference is made to the amount of multivalent metal (as distinct from the source of the metal, such as sodium aluminate), the phr amount refers to the amount of metal itself, rather than the agent or complex that it is part of.

Whilst any amount within this range may be used, in particular embodiments a low amount of multivalent metal is incorporated into the composition. The amount may be within the range of 0.01-0.5 phr. In particular embodiments, the amount of multivalent metal ion is not more than 0.3 phr, preferably less than 0.3. The amount may be 0.29, 0.28, 0.27, 0.26, 0.25, 0.24, 0.23, 0.22, 0.21, 0.20, 0.19, 0.18, 0.17, 0.16, 0.15, 0.14, 0.13, 0.12, 0.11 or 0.10 phr. Using low levels of the multivalent metal (and the multivalent metal source in particular) in the cross-linking composition produces gloves having excellent properties, with low reagent utilisation, as demonstrated in various examples in this specification.

In other embodiments, the amount may be within the broader range of 0.01-1.0 phr, including ranges up to 0.9, 0.8, 0.7, 0.6, 0.5 phr. The amount may in some embodiments be less than 0.4 or 0.3, or 0.25, or 0.2, or 0.15 or 0.1. This contrasts to the typical amount of zinc oxide used in practice in synthetic polymeric products. (Although prior art documents may refer on paper to low levels of ionic cross-linking agent, in practice, films with low solid ionic cross-linking agents do not perform well, and are therefore not commonly manufactured.) The minimum amount may be from 0.02, 0.03, 0.04 or more. The amount used in some embodiments is about 0.05 or about 0.1. Other approximate amounts will be evident from the range of examples shown in this application.

When a multi metal oxide is used as the source of the multivalent metal, the amount of multi metal oxide in some embodiments may be broadly within the range of 0.01-5.0 phr, but in particular embodiments the amount is less than 0.3 phr. The minimum amount may be from 0.01, 0.02, 0.03, 0.04, 0.05, 0.1 or more. The amount used in some embodiments is 0.15 or about 0.5, but in other embodiments the amount used is lower—amounts of about 0.05, 0.08, 0.1, 0.12 or 0.2 are demonstrated in the examples. The maximum amount may be significantly less than 5.0, and may be a maximum of (or less than) 4.0, 3.0, 2.5, 2.0, 1.5, 1.0, 0.9, 0.8, 0.7, 0.6, 0.5, 0.4, 0.3, 0.29, 0.28, 0.27, 0.26, 0.25, 0.24, 0.23, 0.22, 0.21, 0.20, 0.19, 0.18, 0.17, 0.16, or 0.15. Any minimum and maximum may be combined without limitation. In some embodiments, where the degree of carboxylation of the polymer is higher, the amount of multi metal oxide used could be at the higher end of the range. For example, the amount of multi metal oxide as the source for the cross-linking agent could be within one of the following ranges: 0.15 to 5 phr, 1.0 to 5 phr, 2.0 to 4.0 phr, 2.5 to 5 phr or 3.0 to 5.0 phr. In other embodiments, where the degree of carboxylation is low, or there is a high percentage of other polymers that undergo covalent cross-linking (or are self-crosslinkable), the amount of multi metal oxide as the source for the cross-linking agent could be lower. Suitable ranges include 0.01-1.0, 0.01-0.8, 0.01-0.6, 0.01-0.5, 0.01-0.4, 0.01-0.3 or 0.01-0.2. These amounts have been determined using the example of sodium aluminate as the source. To determine the corresponding phr ranges for the multivalent metal per se (to allow for a range to be determined for other sources), the phr values in the ranges shown above for the high-carboxylated polymer and low-carboxylated polymer cases can be multiplied by 33%. It is also acceptable to rely on these phr ranges for any of the different sources of multivalent metal oxides, hydroxides or salts, given the typical relative % amounts of the multivalent metal to other ions in the sources.

Alternatively, one can calculate a particular phr range for a source of the multivalent metal that is other than the metal oxide. To calculate the amount of the source that may be used from the phr ranges provided above for the multivalent metal, one would multiplying the upper and/or lower limits of the particular range by a factor that reflects the % of the multivalent metal in the source. Thus, using the example of alum (containing about 5% aluminium) and the phr range for aluminium of 0.01-0.5, the values are multiplied by 20 to give a phr range of 0.2-10 phr alum.

Preparation of the Cross-Linking Composition

The cross-linking composition is typically formed by solubilising a multimetal oxide of the multivalent metal, a hydroxide of the multivalent metal or a salt of the multivalent metal in water, and controlling the pH to be at least 9.0. Heating may be useful, or necessary, for solubilisation. In the example of sodium aluminate as the multimetal oxide of the multivalent metal, the composition is typically formed by solubilising (or dissolving) sodium aluminate in water with heating.

In some instances, heating can be avoided. However, heating can assist to maximise dissolution. The heating may be to a temperature of at least 35° C., at least 40° C., at least 50° C., at least 80° C. or around 95° C. to boiling. Control of the pH is typically achieved through addition of alkali, as described above, to raise the pH to at least 9.0 (to the specific level set or targeted for the process). The pH may alternatively be adjusted for pH stabilisation at a target pH level. Control of the pH may otherwise be achieved through the use of a multimetal source that has a high pH. Nevertheless, even if the pH is above the required level, it is usually necessary to add further alkali to control the pH more precisely, to allow matching of the pH to that of the aqueous suspension of the synthetic carboxylated polymer. Further, as described above, having a combination of sodium and potassium hydroxide provides advantages when the cross-linking composition and the aqueous suspension of the synthetic carboxylated polymer are combined.

When mechanical stabiliser is used, in accordance with preferred embodiments, the mechanical stabiliser is added to the cross-linking composition to maintain the multivalent metal complex ions in solution, to form a stabilised cross-linking composition, prior to addition of the cross-linking composition to the aqueous suspension of synthetic carboxylated polymer.

In addition to, or in place of, the mechanical stabiliser, a surfactant may be used to improve stability of the cross-linking composition. It is not known to use a surfactant in the preparation of a cross-linking composition in the art of the invention. Whilst surfactants may be added to the latex composition, they are not combined in advance with the cross-linking composition for the purpose of maintaining a multivalent metal in the cross-linking composition in solution as a negatively charged multivalent metal complex ion.

The cross-linking composition needs to be very stable to handle combination into the latex composition in a manner that suits the production of the articles described herein.

Initially, a relatively highly concentrated cross-linking composition can be prepared. Relative amounts of components used in the production of the concentrated cross-linking composition may be, per 100 parts by weight of water:

- Between 0.01 and 5 parts of the (a) multimetal oxide of the multivalent metal, the (b) hydroxide of the multivalent metal or the (c) salt of the multivalent metal (preferably between 0.05 and 3 parts, or between 0.1 and 2 parts);
- Between 0.01 and 5 parts of hydroxide (preferably between 0.05 and 4 parts when using component (a) above, between 0.05 and 3 parts when using component (b) above, or between 0.05 and 4 parts when using component (c) above); and
- Between 0.03 and 15 parts of stabiliser (i.e. total stabiliser, in the case of a mixture; preferably between 0.5 and 3 parts).

There may however be some variation in the amounts shown above—these are indicative values that have been shown to work effectively.

After forming of the concentrated composition, this may be diluted prior to addition of the cross-linking composition to the aqueous suspension of a synthetic carboxylated polymer. The dilution is usually performed to reduce the concentration such that the multivalent metal ion concentration is reduced to between 0.33-3.3% by weight of the cross-linking composition. In this case, the amount is based on the metal ion, rather than the total weight of the source of multivalent metal ions (a), (b) or (c). If considering the amount of the multivalent metal source (i.e. (a), (b) or (c)) in the diluted cross-linking composition, the diluted concentration of the source is typically between 1-10% by weight of the cross-linking composition. As one example, the diluted concentration of sodium aluminate in the cross-linking composition may be about 5% (about 1.5% aluminium). The initial concentration of multivalent metal ions based on the above typical amounts in the concentrated cross-linking composition is around 3 to 10% by weight.

Elastomeric Article-Forming Composition

The elastomeric article-forming composition comprises the cross-linking composition, as described above, and a synthetic carboxylated polymer. The polymer is in the form of an aqueous suspension. The aqueous suspension has a pH of at least 9.0. The elastomeric article-forming composition is also referred to as the "synthetic latex composition" or "latex composition", as a short-hand reference. It is common in the art to use the expression "latex" or "rubber" to refer to any polymer in a general sense, and "latex composition" is used in a corresponding manner. Latex is not to be read as referring to natural rubber latex. Accordingly, particularly in the examples which follow, it should be understood that these terms have been used as short-hand to refer to the polymer of the composition.

The inventors found when performing their test work that the best results are obtained when a shock-increase in the pH of the latex composition (i.e. the aqueous suspension of the synthetic carboxylated polymer, as it is combined with other components to produce the latex composition) is avoided. This can be achieved in two ways. One way involves very slow addition of the cross-linking composition to the aqueous suspension of the synthetic carboxylated polymer, to allow for equilibration of the pH without a shock increase in pH. (It is noted that the higher the pH and concentration of the cross-linking composition, the slower the addition rate, and vice versa.) The second alternative is to ensure that the pH of the cross-linking composition is reasonably "matched" to the pH of aqueous suspension of the synthetic carboxylated polymer. If the pH's are not too far apart, then the rate of addition is not as critical. Ideally, the matching involves bringing the pH of both components (or streams) within 1.0 units, or between 0.5 units of each other, preferably within 0.2 units of each other, and most preferably the same pH. However, as noted above, an even higher pH difference is permissible if there is very slow addition if the cross-linking composition stream, and the cross-linking composition added is suitably stabilised with mechanical stabiliser and/or surfactant. By adding the cross-linking composition as a diluted stream, at a slow rate of addition and/or with a matched pH, it is possible to produce a latex composition from which there is no, or minimal, precipitation of the multivalent metal. (That is, there is less than 20%, less than 15%, less than 10%, less than 5%, less than 2% and preferably no precipitation of the multivalent metal from the latex composition).

Supply of an aqueous suspension of a synthetic carboxylated polymer to a manufacturing facility is usually in the form of a concentrated solution, with a pH below 9.0. In the method of the invention, it may be necessary to add alkali to the aqueous suspension of the synthetic carboxylated polymer prior to the addition of the cross-linking composition to raise the pH of the aqueous suspension to at least 9.0. Alkali is referred to below in the list of other components that may be present in the latex composition, as a stabiliser. The amount should be controlled to ensure the required pH for the aqueous suspension.

It may also be necessary to dilute the supplied aqueous suspension of synthetic carboxylated polymer to a total solids content (TSC) that is closer to that required in the production of the elastomeric articles. For dipped articles, the final dipping TSC may be around 5-40%, and in some cases for thin film products, it may be between 5% and 25%, or between 5% and 20%. The initial dilution will be to a TSC that is a little higher than the final dipping TSC concentration. The supplied aqueous suspension of synthetic carboxylated polymer TSC typically needs to be at least about 5% higher than the TSC at which dipping is performed, in view of the fact that the composition will be diluted through the addition of the aqueous form of cross-linking composition of the present invention. Supplied latex may be provided at a TSC of around 45%, around 50%, around 55% or around 60%, in some examples. The TSC at which the articles are formed (for example, the dipping or dipping composition TSC) may therefore be between 5-40%, 5-45%, 5-50% or 5-55%, respectively, for such supplied latex compositions.

Synthetic Carboxylated Polymer

The polymer used in the present application is a carboxylated polymer. The polymer is also synthetic, in that natural rubber (natural isoprene) is not within the range of polymers to which the invention applies.

The synthetic carboxylated polymer may be selected from the group consisting of carboxylated nitrile butadiene rubber, carboxylated styrene butadiene rubber, carboxylated butyl rubber, carboxylated acrylic butadiene rubber, carboxylated polyisoprene, carboxylated polychloroprene, and mixtures or copolymers thereof. In some embodiments, the synthetic carboxylated polymer is carboxylated acrylonitrile butadiene polymer, or a co-polymer of this polymer, or a mixture of this polymer with a second polymer. In other embodiments, the synthetic carboxylated polymer is a carboxylated synthetic butadiene/chlorobutadiene polymer.

Carboxylated refers to the presence of carboxylate (carboxylic acid or ester) groups on the polymer chain. Carboxylation may be achieved by forming the polymer with a monomer containing carboxylate groups, or through grafting carboxylate groups to a polymer. As examples of suitable carboxylated polymers, reference is made to PCT/AU2014/000726 and PCT/AU2014/000727, the entirety of each being incorporated into this specification by reference.

As indicated below, the degree of carboxylation of the polymer may influence the decision as to whether a second cross-linking agent is required. Where the carboxylation degree is 5-15% (more typically 5-10%), then ionic cross-linking as provided by the cross-linking composition of the invention may be sufficient to achieve the desired degree of cross-linking and film properties. Thus, sulphur-free and/or zinc-free articles may be produced. Where the carboxylation degree is lower, for example between 0.01-5%, then a second cross-linking agent may be desirable. For calculating the % carboxylation, reference is made to the above PCT publications. For mid-range carboxylation, the choice can be made to have solely ionic cross-linking s provided by the cross-linking composition, or to have a second cross-linking agent too. Different embodiments take into account the different desired properties of the final article.

Adding of the Cross-Linking Composition to the Polymer Suspension

The cross-linking composition may be added to the aqueous suspension of the polymer in an amount of between about 0.01 and 0.5 parts per 100 parts by volume of the aqueous suspension of the synthetic carboxylated polymer. The cross-linking composition is very dilute, so a relatively high volume of dilute cross-linking composition is required. This is another factor found to aid in the formation of a stable latex composition. The typical amount is amount in some embodiments is between 0.03 and 0.3 parts (per 100 parts synthetic polymer suspension), and in some cases between 0.03 and 0.1 parts.

Prior to, or at the same time that the cross-linking composition is added, it is advantageous to add surfactant to the aqueous suspension of synthetic carboxylated polymer. This aids to maintain the stability of the emulsion and the stability of the multivalent metal complex ions in solution. Such surfactants are additional to those that may be used in the formation of the cross-linking composition, which may also be selected from the examples set out below.

The surfactant may be selected from anionic surfactants, non-ionic surfactants, and combinations of agents from one or both classes.

Suitable anionic surfactants include, but are not limited to, ($C_8$-$C_{18}$) alkyl sulfates, ($C_8$-$C_{18}$) linear alkyl aryl sulfates, ($C_8$-$C_{18}$) alkyl ether sulfates, ($C_8$-$C_{18}$) fatty acid salts, ($C_8$-$C_{18}$) alkyl ether sulfates having one or more moles of ethoxylation, ($C_8$-$C_{18}$) alkyl ether sulfonates, sulfate esters of an alkylphenoxy polyoxyethylene ethanol, ($C_8$-$C_{18}$) alkamine oxides, ($C_8$-$C_{18}$) alkoyl sarcosinates, ($C_8$-$C_{18}$) sulfoacetates, ($C_8$-$C_{18}$) sulfosuccinates, ($C_8$-$C_{18}$) alkyl diphenyl oxide disulfonates, methyl ester sulfonates, alpha-olefin sulfonates, alkyl carbonates, alkyl ether carboxylates, fatty acids, sarcosinates, octoxynol or nonoxynol phosphates, taurates, fatty taurides, fatty acid amide polyoxyethylene sulfates, isethionates and or blends thereof. ($C_8$-$C_{18}$) alkyl group may be straight chain (e.g., stearic, cetyl, lauric, oleic, myristic) or branched (e.g. 2-ethylhexyl). The cation of the anionic surfactant may be an alkali metal (e.g., sodium or potassium), ammonium, $C_1$-$C_4$ alkylammonium (e.g., mono-, di-, tri-), or $C_1$-$C_3$ alkanolammonium (e.g., mono-, di-, tri-). The specific examples of such anionic surfactants include, but are not limited to, lauryl sulfates, octyl sulfates, 2-ethylhexyl sulfates, dodecyl benzene sulfonates, lauramine oxide, decyl sulfates, tridecyl sulfates, cocoates, lauryl sarcosinates, lauryl sulfosuccinates, lauryl ether sulfates (one or more ethylene oxides), myristyl sulfates, oleates, stearates, tallates, ricinoleates, cetyl sulfates and so forth.

Non-ionic surfactants include the following non-exhaustive examples: ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and blend thereof. Specific examples, but are not limited to, methyl gluceth-10, PEG-20 methyl glucose distearate, PEG-20 methyl glucose sesquistearate, $C_{11-15}$ pareth-20, ceteth-8, ceteth-12, dodxpol-12, laureth-15, PEG-20 castor oil, pollysorbate-20, steareth-20, polyoxyethylene-10 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, oxyethanol, 2,6,8-trimethyl-4-nonyloxypolyethyleneoxyethanol, alkyleneoxypolyethylene-oxyethanol, alkyleneoxypolyethyleneoxyethanol water soluble alcohol ethylene oxide condensates with $C_8$-$C_{18}$ carbon atoms in a straight or branched chain configuration with 5 to 30 moles of ethylene oxide and blends thereof. Other suitable nonionic surfactants include the polyethylene oxide condensates of one more of alkyl phenol containing $C_8$-$C_{18}$ carbon atoms in a straight or branched chain configuration with 5 to 30 moles of ethylene oxide and blends thereof. Specific examples of alkyl phenol ethoxylates include nonyl condensed with about 7-13/9.5 moles of ethylene oxide per mole of octyl/nonyl phenol, dinonyl phenol condensed with about 12/15 moles of EO (ethylene oxide) per mole of phenol and mixtures thereof.

The surfactant is typically added as an aqueous solution. The solution concentration is typically around 2-10%. The amount of surfactant solution that may be added to the aqueous suspension of the polymer with the cross-linking composition may be such as to provide 0.01-5 phr to the latex composition. The range may be between 0.1-2 phr, or about 0.6 phr. It is noted that this surfactant is additional to any surfactant that may be present in the concentrated aqueous suspension of synthetic carboxylated polymer supplied by the supplier.

Other Components Added to Form the Elastomeric Article-Forming Compositions

Other components may be added to the latex composition, in addition to the cross-linking composition and the surfactant. These other components may include components selected from the group consisting of second cross-linking agents, plasticizers, anti-ozonants, stabilisers such as pH stabilisers, emulsifiers, antioxidants, vulcanising agents, polymerisation initiators, pigments, fillers, colourising agents and sensitisers. Many of these agents are added in particulate form. Others are added as liquids. These are added prior to forming the latex composition into the shape of the synthetic elastomeric article. In some embodiments they are added at the same time as the cross-linking composition. In other embodiments, they are added after.

Second Cross-Linking Agent

Although in some embodiments it is possible to use the cross-linking composition containing solubilised multivalent metal as the only cross-linking agent, in other embodiments a second cross-linking agent will be added. This is added as a separate component during the formation of the latex composition. This is typically added as a solid, particularly in the case of ionic cross-linking agents and sulphur. The particulate cross-linking agents may be added to the aqueous suspension of the synthetic carboxylated polymer at the same time as the cross-linking composition, or following addition of the cross-linking composition.

The multivalent metal of the cross-linking composition provides ionic bonding only, so in some embodiments, to provide covalent bonding, sulfur and sulfur donating cross-linking agents are recommended as second cross-linking agents. Such covalent bonding may provide water resistant characteristics due to its hydrophobic nature and will have more endurance at aqueous conditions. Thus, where the degree of carboxylation is low, a covalent cross-linking agent may be desired.

The second cross-linking agent may be a single type of cross-linking agent, or there may be more than one such second cross-linking agent. Each may be referred to as a second cross-linking agent, or they may be referred to as a second, third (and optionally further) cross-linking agents.

The covalent cross-linking agent may be selected from the covalent cross-linking agents, including organic cross-linking agents, sulphur and/or sulphur donors, and combinations thereof.

The cross-linking agents may be selected from the above described covalent cross-linking agents, ionic cross-linking agents, and combinations thereof.

Amongst the range of cross-linking agents, the following may be used in embodiments of the invention:

Sulphur may be added in the form of elemental sulphur. Sulphur donors are another way of providing sulphur cross-linking. Sulphur donors release sulphur, or act with sulphur-containing compounds, to accelerate sulphur-based covalent cross-linking of the elastomer-forming polymer. Generally, sulphur donors can be advantageous as they shorten the curing (vulcanisation) time, lower the curing temperature or decrease the amount of cross-linking agents required to be used in the composition. However, on the negative side, sulphur donors can give rise to allergic reactions, such as allergic contact dermatitis with symptoms including erythema, vesicles, papules, pruritus, blisters and/or crusting. Examples of suitable sulphur donors include the carbamates such as thiocarbamates (e.g. zinc dibutyl dithiocarbamate (ZDBC), Zinc diethyl dithiocarbamate (ZDEC); Zinc dimethyl dithiocarbamate (ZDMC); thiurams (eg. tetraethylthiuram disulfide (TETD), Tetramethylthiuram disulphide (TMTD)); Dipentamethylene thiuram tetrasulfide (DPTT); Dipentamethylene thiuram hexasulfide (DPTH); Dipentamethylene thiuram hexasulfide; thiourea (Ethyl thiourea (ETU) and diphenylthiourea (DPTU); thiazoles (e.g. Mercapto Benzothiazoles (MBT), Mercapto Benzothiozole disulphide (MBTS), zinc 2-mercaptobenzothiazole (ZMBT)); guanidines (eg. Diphenylguanidine (DPG)) and aldehyde/amine-based sulphur donors (eg. hexamethylenetetramine). Other examples are well known in the art and can be obtained from various publicly available sources.

In some notable embodiments, the second cross-linking agent comprises either (a) sulphur and a sulphur donor, (c) sulphur and a sulphur donor together with an ionic cross-linking agent, or (d) a sulphur donor. In these embodiments, the second cross-linking agents may consist of these cross-linkers as the only additional cross-linking agents. (In that case, the cross-linking composition may comprise the solubilised multivalent metal oxide, hydroxide or salt, as the only cross-linking agents of said cross-linking composition. Further, in example (a), the composition is free of solid metal oxide cross-linking agent, and in the case of (d), the composition may be free of sulphur and free of solid metal oxide cross-linking agent). In another embodiment, the second cross-linking agent comprises (b) a multivalent metal oxide or ionic cross-linking agent. In this embodiment, the product is free of sulphur and sulphur donor.

In other embodiments, other cross-linking agents that are suitable for use in the elastomeric film-forming composition are selected from, but are not restricted to crosslinking monomers, reactive oligomers, polyisocyanate oligomers, functional, crosslinkable polymers, derivatives of ethylene glycol di(meth)acrylate (such as ethylene glycol diacrylate, di(ethylene glycol) diacrylate, tetra(methylene/ethylene glycol) diacrylate, ethylene glycol dimethacrylate (EDMA), di(ethylene glycol) dimethacrylate (DEDMA), tri(methylene/ethylene glycol) dimethacrylate, tetraethylene glycol dimethacrlate (TEDMA)), derivatives of methylenebisacrylamide (such as N,N.-methylenebisacrylamide, N,N.-methylenebisacrylamide, N,N.-(1,2 dihydroxyethylene)bisacrylamide), formaldehyde-free crosslinking agents (such as N-(1-Hydroxy-2,2-dimethoxyethyl)acrylamide), divinylbenzene, divinylether, diallyl phthalate, divinylsulfone, Trimethylolpropane Trimethacrylate (TMPTMA) and the like. Some of these cross-linking agents are commercially available and are supplied by companies such as Aldrich. Combinations of these cross-linking agents can also be used.

To get the better uniformity of the film and properties thereof and poly functional cross linkers could also be used, some poly functional cross linkers are (but not limited to) diphenylmethane-bis-4,4'-N-ethylene urea, N,N'-1,6-hexanediylbis-1-aziridinecarboxamide, pentaerythritol tris (3-(1-aziridinyl) propionate, trimethylolpropane tris (2-methyl-1-aziridine propionate, trimethylolpropane-tris-(B—N-aziridinyl) propionate, multifunctional methacrylate monomers like ethylene glycol dimethacrylate, triethylene glycol dimethacrylate, trimethylolpropane trimethacrylate—simple organic cross linkers like water soluble glyoxal could be used—these will improve adhesion of water based systems to non-polar substrates at molecular level and thereby making the film formation better and free from cracks.

Solid ionic cross-linking agents are another class that may be added. This class includes solid metal oxide cross-linking agents, such as zinc oxide and magnesium oxide. In some (but not all) embodiments, they are avoided (thus, zinc oxide may be avoided), to avoid the costs and disadvantages described previously. However, when used in low amounts, they can provide additional properties that may be useful in some applications. Metal oxides (particularly when used in solid form) are typical examples, including zinc oxide and magnesium oxide. Peroxides also form ionic cross-links. An example of a peroxide cross-linking agent is 1,1-di(t-butylperoxy)-3,3,5-trimethylcyclohexane, which can be purchased under the trade name Trigonox 29-40B-pd. Other ionic cross-linking agents amongst those known in the art can be used.

When a second cross-linker is present, in some embodiments, this is selected from the group consisting of sulphur, organic peroxide, organic cross-linkers, sulphur donors and combinations thereof. This grouping excludes the solid inorganic ionic cross-linkers.

In embodiments shown to have particular utility in commercial production, the second cross-linking agent may be selected from either:
(a) sulphur and a sulphur donor,
(b) a multivalent metal oxide or ionic cross-linking agent (zinc oxide being a notable example),
(c) sulphur, a sulphur donor and an ionic cross-linking agent, or
(d) a sulphur donor.

The examples show the utility of these cross-linking agents as the only cross-linking agents used in combination with the cross-linking composition. In such cases, other cross-linking agents may be avoided, but small amounts (below 0.01 phr) should not be considered to avoid the scope of such a claim.

Amounts of Second Cross-Linkers

In broad terms, any amount of second cross-linker may be used, as required for the final article properties. Thus, the total amount of cross-linking agents in the composition (including that added in the formation of the cross-linking composition) may be between 0.01 and 14 phr. However, it is usually desirable to minimise cross-linker amounts (and the associated costs or disadvantages). With the use of the cross-linking composition of the present invention, this is possible. The total cross-linking agent amount (including that used to form the cross-linking composition) may be within one of the following ranges: 0.01-14.5 phr, 0.2-12.5 phr, 0.3-10 phr, 0.1-10 phr, 0.2-10 phr, 0.3-9 phr, 0.5-9 phr, 0.8-9 phr, 0.3-8 phr, 0.5-8 phr, 0.8-6 phr, 1-5 phr, 2-9 phr, 3-10 phr, 3-7 phr, 1-3 phr, 0.01-0.5 phr, 0.01-1.0 phr.

In desirable embodiments, the amount of each secondary cross-linker is preferably not more than 1.0 phr, preferably not more than 0.9, 0.8. 0.7, 0.6, 0.5, 0.4, 0.3 or 0.2 phr. The total amount of all secondary cross-linkers is preferably also not more than (or is below) 1.0, 0.9, 0.8. 0.7, 0.6, or 0.5 phr.

The amount of sulphur, when used as a second cross-linker, may be between 0.0-5.5 phr. The amount may be lower still, at 0.0-3.5 phr, such as 0.01-3.0 phr, 0.01-2.0 phr, 0.01-1.5 phr, 0.01-1.0 phr or 0.01-0.5 phr. The amount is preferably not more than 1.0 phr, preferably not more than 0.9, 0.8. 0.7, 0.6, 0.5, 0.4, 0.3 or 0.2 phr.

The amount of sulphur donor, when used as a second cross-linker, may be between 0.0-2.0 phr, such as between 0.1-1.5 phr, 0.1-1.0 phr, 0.2-1.0 phr, 0.3-2.0 phr, 0.3-1.5 phr or 0.2-0.6 phr. The amount is preferably not more than 1.0 phr, preferably not more than 0.9, 0.8. 0.7, 0.6, 0.5, 0.4, 0.3 or 0.2 phr.

The amount of organic cross-linking agent, when used as a second cross-linker, may be between 0.0-4.0 phr, such as 0.01-4.0. The amount may be lower still, at 0.01-3.0 phr, or 0.01-2.0 phr, or 0.01-1.0 phr.

The amount of ionic cross-linking agent, when used as a second cross-linker, may be between 0.0-4.0 phr, such as 0.01-4.0. The amount is preferably lower still, at 0.01-3.0 phr, or 0.01-2.0 phr, 0.01-1.0 phr or 0.01-0.5 phr. This applies to solid multivalent metal oxides such as zinc oxide. The amount is preferably not more than 1.0 phr, preferably not more than 0.9, 0.8. 0.7, 0.6, 0.5, 0.4, 0.3 or 0.2 phr.

Other Components

Stabilisers may be used in the elastomeric article-forming composition. The stabilizer may be, for example, an anionic surfactant and or other non-ionic surfactants. The elastomer-forming polymer can be diluted with a solution of a stabilizer, such as potassium hydroxide, ammonium hydroxide and/or sodium hydroxide. The amount of stabiliser used is dependent on the polymer used in the elastomeric film-forming composition, the pH of the composition and other factors. The stabiliser can range from 0.1-5.0 phr, e.g. 0.5 to 2 phr, preferably 1.0 to 1.5 phr, which is diluted with water, preferably filtered water- or de-ionized water, or water having a total solid content of around 5 ppm level.

Emulsifiers may be used in the elastomeric article-forming composition. Suitable emulsifiers include comprise sodium alkyl aryl sulphates, sodium alkyl sulphates or other anionic/non-ionic surfactants. The amount of emulsifier used is dependent on the on the polymer used in the elastomeric film-forming composition, the pH of the composition and other factors. The amount of emulsifier can range from about 0.1 to 3 phr.

pH stabilisers may be used to avoid the possibility of destabilization, which is possible where the polymer contains carboxylic acid groups. Suitable pH stabilisers include potassium hydroxide, ammonium hydroxide and/or sodium hydroxide. Preferably, the pH stabiliser is potassium hydroxide. A diluted stabilizer solution can be mixed with the polymer. The pH of the mixture is suitably adjusted to between about 8.5 to about 12.5, or between about 8.5 to about 11.0. The cross-linking agent(s) can then be added to the mixture.

Anti-ozonants may be used in the elastomeric article-forming composition. Suitable anti-ozonants include paraffinic waxes, microcrystalline waxes and intermediate types (which are blends of both paraffinic and microcrystalline waxes). The amount of anti-ozonant can range from about 0.0 to 5.0 phr.

Antioxidants may be added to the elastomeric article-forming composition of the present invention. Suitable antioxidants include hindered arylamines or polymeric hindered phenols, and Wingstay L (the product of p-cresol and dicyclopentadiene). The antioxidant may, for example, be added in an amount ranging from 0.0-5.0 phr, 0.0-3.0 phr, 0.0-1.0 phr or 0.3-0.5 phr.

Pigments such as titanium dioxide, selected for its pigmentation, to reduce the transparency of the final elastomeric film, may be added in amounts ranging from 0.01-10.0 phr, such as 1.5-2.0 phr or 1.0-3.0 phr and colorants can also be added in the desired amounts. The mixture is then diluted to the target total solids concentration by the addition of a liquid, such as water. The pigments used in the elastomeric film-forming composition may be selected from the group consisting of EN/USFDA approved dyes.

Rubber reoderants may be used in the elastomeric article-forming composition. Suitable rubber reoderants include perfume oils of natural or synthetic origins. The amount of rubber reoderant can range from about 0.001 to 2.0 phr.

Wetting agents may be used in the elastomeric article-forming composition. Suitable wetting agent emulsifiers include anionic surfactants like sodium dodecyl benzene sulfonate or sodium lauryl ether sulfate, or non-ionic ethoxylated alkyl phenols such as octylphenoxy polyethoxy ethanol or other non-ionic wetting agents. The amount of wetting agent can range from about 0.001 to 2.0 phr.

Defoamers may be used in the elastomeric article-forming composition. Defoamers may be chosen from naphthalene type defoamers, silicone type defoamers and other non hydrocarbon type defoamers or defoamers of refined oil of vegetable origin. The amount of defoamers can range from about 0.001 to 2.0 phr.

The elastomeric article-forming composition could also be blended with inorganic filler. Suitable inorganic fillers include calcium carbonate, carbon black or clay. Preferably, the amount of inorganic filler included in the blend would not exceed 75% either alone or in combination. It will be appreciated that the blended composition will retain the favorable properties.

The elastomeric article-forming composition comprising carboxylated synthetic polymer more specifically and multi metallic oxide and additives thereof could also be blended with another alternative elastomer. For example, the alternative elastomers, for specific intended application like physical properties, permeation characteristics, film uniformity. Examples of suitable alternative elastomers include styrene butadiene rubber and butyl rubber, polyisoprene and mixtures thereof. Preferably, the amount of alternative elastomers included in the blend would not exceed 95% either alone or in combination. In some embodiments, an elastomer is present in an amount of from 0 to 95%. The range could be 0-5%, 5-10%, 10-15%, 15-20%, 20-25%, 25-30%, 30-35%, 35-40%, 40-50%, 50-60%, 60-75%, 60-80%, 70-90% or 80-95%. It will be appreciated that the blended composition will retain the favourable intended properties to the applications concerned.

Sensitisers are chemicals that can be used in compositions for producing elastomeric films to control the amount of the composition that will remain coated on the mould during dipping (film deposition). Examples of sensitisers known in the art that can be used in the composition for producing an elastomeric film include polyvinyl methyl ether, polypropylene glycol, ammonium nitrate and ammonium chloride. When used, the amount of sensitiser will be chosen based on the desired film thickness to remain on the mould during dipping, and will generally be between 0.01-5.0 phr. For thinner films, the amount will generally be between 0.01 to 2.0 phr, e.g. 0.1 to 1.0 phr. When other techniques are used for controlling the film thickness on the mould, such as the use of pre-dipping the mould into coagulant before undertaking the multiple dipping into the composition for producing the elastomeric film, the composition for producing an elastomeric film may not require a sensitiser.

Those skilled in the art will readily be able to vary the components of the elastomeric article or film-forming composition to suit the particular polymer used as well as the particular final article desired. It will also be understood by those of skill in the art that specific chemicals or compounds which have been listed above are intended to be representative of conventional materials that may be used in formulating the elastomeric film-forming composition and are merely intended as non-limiting examples of each such component of the composition.

The elastomeric article-forming composition is preferably formalin-free.

Final Composition Preparation Stages

The steps in the production of the cross-linking agent, and the main steps in the formation of the latex composition, have been described above. In other respects, the process steps for the production of the article are as known or practiced in the art.

By way of additional comment, it is noted that in the case of the present invention, the cross-linking composition provides the multivalent metal in a solubilised form, and any second cross-linkers which are in solid form are added following milling. Milling is performed using suitable milling equipment to reduce the particle size to a suitable range. Preferably, the average particle size is below 5 microns. Uniform particle size is desirable, and coarse milling may result in non-uniform particles and therefore a non-uniform film, which can result in high fluctuation in film properties.

After the desired pH is reached for the aqueous polymer suspension (above 9.0, such as 9.0 to 12), the cross-linking composition is added. Any shock increase in the pH during addition of the cross-linking composition will result in coagulation from micro level to the macro level.

When the components have been mixed uniformly or to homogeneity, other additives such as pigments and colorants are added. The elastomeric article-forming composition is then left for maturation. The length of the maturation may vary depending on the level of cross-linking agent and the degree of carboxylation of the polymer. The cross-linking composition-containing suspension of the carboxylated synthetic polymer does not require lengthy maturation since the condensation reaction is theoretically rapid. However, the composition may be left for a minimum of 2 to 18 hours for the purpose of removing air bubbles inside the compounded polymer. In some cases maturation could be conducted over a longer period depending upon the requirements for preparing the article and the level of cross-linking agents present. The compounded elastomeric film composition with suitable additives could be prematured (in view of other crosslinkers involved in the composition) by holding the composition at a controlled elevated temperature. For example, the elastomeric article-forming composition could be held at 40° C. to 60° C. for a period of, for example, about 4 hours to about 24 hours depending on the temperature, degree of carboxylation of the polymer, the amount and type of vulcanization activators and sulphur donors, and type and quantity of pH stabilizer and emulsifier stabilizer and wetting agents/surfactants.

Preparation of Elastomeric Articles, Such as Films

The composition is formed into the shape of the desired article, and then cured. Curing is used in a general sense, to refer to the stage during which cross-linking is performed. The curing step includes the process of cross-linking of the multivalent metal in the cross-linking composition with the carbon/late groups of the polymer. Other curing conditions may apply, such as the conditions required for curing the second cross-linking agents. Such conditions are as known in the art.

The forming of the product into the desired shape may involve moulding into a mould, depositing the composition onto a surface, or dipping of a former into the composition. The composition is particularly suited to dipping applications. Films can be produced by dipping, and gloves in particular. Thin film gloves are a desirable product.

The steps in the manufacture of a film, as an example of an article that may be formed from the composition, film are as generally described in PCT/AU2014/000726 and PCT/AU2014/000727, other than the film compositions.

The basic process steps in some embodiments are as follows:

Optional Step (a) Dipping the Former into a Coagulant Containing Multivalent Ions in Solution The details of this step are as described in the PCT publications referred to above. In brief, a suitable former, which is based on the shape of the article to be produced (e.g. flat for a film or glove-shaped for a glove) can be dipped into a coagulant containing multivalent ions in solution. The former is dipped into a coagulant containing multivalent ions, leaving a thin coating of the charged ions on the surface of the former. The charged ions coating can assist in controlling the amount composition for forming the elastomeric film that will subsequently remain on the surface of the mould after dipping into the composition, through charge interactions. The composition of the coagulant may be as described in the two PCT publications as described above. Cationic multivalent ion-containing coagulants are typically used, such as a calcium coagulant.

Optional Step (b) Drying or Partially Drying the Coagulant-Dipped Former

If the former is dipped into a coagulant, following this step the former is dried or partially dried.

Step (i) Dipping the Former into the Elastomeric Article-Forming Composition of the Invention to Produce a Layer of Elastomeric Article-Forming Composition on the Mould The former is dipped into the composition for producing an elastomeric film, embodiments of which have been described in detail above. The duration of dipping, temperature, and former surface temperature may be as described in the PCT publications referred to above.

Step (ii) Drying or Partially Drying the Layer of Elastomeric Film-Forming Composition on the Former The conditions and details of this step may be as described in the PCT publications referred to above.

The method of manufacture described herein encompasses the preparation of single-layered or multiple-layered elastomeric films. Therefore, in some embodiments, the method may include step (v), which involves drying and curing the layered elastomeric film on the former directly after this step to prepare a single layered elastomeric film. In other embodiments, the method may include a number of repetitions of optional steps (iii) and (iv) after this step to produce a multiple-layered elastomeric film.

Step (iii) Optionally Dipping the Former Coated with the Dried or Partially Dried Layer of Elastomeric Film-Forming Composition into the Elastomeric Film-Forming Composition to Produce a Further Layer of Elastomeric Film-Forming Composition on the Former This step is optional, and is present when multi-layer articles are produced. The details of this step are as described in the PCT publications referred to above.

Step (iv) Optionally Repeating the Drying or Partial Drying Step (ii) and the Further Dipping Step (iii)

This step is optional, and is present when multi-layered articles are produced. The number of layers may be 2, 3 or more in multi-layered articles. The details of this step are as described in the PCT publications referred to above.

Optional Additional Steps Prior to Drying and Curing

Further steps can be taken to fine-tune the manufacture of the elastomeric film or article. The details of these steps are as described in the PCT publications referred to above. In brief, the film or article can be leached to remove extractable components, there may be a coating material applied, beading/cuffing cab be performed and/or the product may be passed through a curing or vulcanizing oven to evaporate the water in the film and enable better cross linking.

Step (v) Drying and/or Curing the Layered Elastomeric Film on the Former

The details of this step are as described in the PCT publications referred to above.

Optional Additional Steps Following Drying and Curing

This step is optional. The details of this step are as described in the PCT publications referred to above. These optional steps include cooling, chlorination, post-curing rinsing, polymer coating and additional drying steps, prior to stripping the article from the former. The cured film may also be cooled/chlorinated/neutralized—post-leached in hot water and optionally dipped in lubricant solution or any silicone/silicone free polymers to enable easy stripping and better donning.

The film or article is stripped from the former at the conclusion of the formation process.

Articles Produced from the Elastomeric Film-Forming Composition

The elastomeric article-forming composition of the present invention can be used to prepare a variety of articles, including dipped articles in particular. Examples of possible articles include surgical and examination gloves, industrial gloves, finger cots, catheters, tubing, protective coverings, balloons for catheters, condoms, industrial gloves, laboratory gloves, household gloves, gardening gloves, electrical gloves, irradiation gloves, finger cots, weather balloons, clean room gloves for electronic industries, gloves for food contact and food processing and biotechnical application and the like.

The thickness of the final film (or article) can, for example, be in the range 0.01-3.0 mm, such as 0.01-0.3 mm, less than 0.25 mm, less than 0.24 mm, less than 0.23 mm, less than 0.22 mm, less than 0.21 mm, less than 0.2 mm, 0.02-0.2 mm, less than 0.19 mm, less than 0.18 mm, less than 0.17 mm, less than 0.16 mm, less than 0.15 mm, 0.05-0.10 mm, 0.03-0.08 mm, or 0.05-0.08 mm (for thin or disposable gloves), and 0.2-3.0 mm for thick gloves. The thickness is suitably measured as an "average thickness", particularly for gloves, using the points of measurement described below. The points of measurement are at three points in the glove, and an average of the three values may be taken for the (average) film thickness. A corresponding technique can be used for non-glove articles, such as condoms. In some embodiments, the film thickness of a glove is less than 2 mm (e.g. from 0.01 mm to 2 mm). For example, the film thickness may be in the range of from 0.04 mm to 2 mm. In another embodiment, the glove may have a weight of about 4 grams, or about 3 grams, while it will be appreciated that higher and lower glove weights may also be obtained depending on the purpose for which the glove is to be used. The weight may be, for instance not more than 5 grams, not more than 4.9, 4.8, 4.7, 4.6, 4.5, 4.4, 4.3, 4.2, 4.1 or 4.0 grams on average. This calculation may be based on a sample of at least 10 gloves.

The final film (or article) can, for example, have one layer or be made from multiple layers produced by subsequent dipping steps. For example, the final film (or article) may comprise from 1 to 15 layers.

The final film prepared from the elastomeric film-forming composition of the invention retains the favourable feel and comfort that is closer to natural rubber film yet is free of proteins and other potential allergens (causing Type I allergy) associated with natural rubber. In some embodiments, the final film prepared from the elastomeric film-forming composition of the invention has reduced skin irritation compared to natural rubber film. For example, the final film prepared from the elastomeric film-forming composition of the invention reduces the risk of Type I allergy compared to natural rubber film. Preferably, the film prepared from the elastomeric film-forming composition of the invention avoids Type I allergy. Where the dipped article is a glove, retaining the properties of natural rubber gloves also means that the products are easily donnable without any visible powder anti tack material. Like natural rubber gloves, the gloves of the present invention could be easily donnable without any visible powder anti tack material like talc, corn starch or calcium carbonate however contains polymeric laminate of acrylate on the interior surface of the glove or chlorinated. However production of pre-powdered article is also possible with the less amount of powder content required by the standard concerned or the customer requirement. Further, proper curing of the film removes tackiness, and the bonding characteristics of the polymer comprising base polymer unit/s acrylonitrile butadiene, styrene butadiene, chlorobutadiene—one or more carboxylic acid residues or esters thereof makes the common coating material sufficient enough for proper donning and non-tacky effect and suitable powder free conditions.

The articles produced by the method have a desirable balance of properties. In typical embodiments, the articles have a modulus at 500% of less than 7 MPa. The modulus at 500% may be not more than (or less than) 6.5 MPa, or even less than 6.4, 6.3, 6.2, 6.1, 6.0 or lower. This value may be based on the unaged variant, but is preferably based on the aged variant, or both the unaged and aged variants. Having such a low modulus, in combination with a thin glove (e.g. one of the values indicated above, such as 0.2 mm or less), is an excellent achievement for such gloves. The articles may have an elongation at break of at least 700%. The articles of typical embodiments have these properties combined. In some embodiments, the article is chloroprene-free, and has a modulus at 500% of less than 7 MPa (or less than 6.5) and an elongation at break of at least 700%. IN other embodiments, there is provided articles, such as gloves, with an elongation at break of at least 700% combined with thin film thickness (of 0.2 mm or less). The production of articles with these properties, particularly with low (or no) second cross-linking agents, is a notable feature of embodiments of the present invention.

In the claims and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

EXAMPLES

The invention will now be described in further detail with reference to the following non-limiting examples which involve the preparation of elastomeric film gloves as the elastomeric articles.

General Procedure for Production of Elastomeric Articles

In the examples set out below, the following general procedure was utilised to produce elastomeric gloves, unless indicated to the contrary.

1. Preparation of Cross-Linking Composition

One part sodium aluminate as the chosen multivalent metal source, together with 1 part sodium hydroxide and 1 part potassium hydroxide as alkali and 1 part glycerine as stabiliser, were combined with 46 or 96 parts water, depending on the example. The combination was heated at an elevated temperature (typically around 95° C., but anywhere from 80° C. to boiling point) to dissolve the multivalent metal, through the formation of negatively charged multivalent metal complex ions. The concentration of metal ions in the cross-linking compositions obtained was 0.66% or 0.33% by weight of total solution, respectively. The pH of the solution was in the range of about 12-13.

2. Preparation of Latex Composition

A commercially-available aqueous suspension of synthetic carboxylated polymer, supplied at a total solids content of about 45%, is diluted to an intermediate total solids content using 3% potassium hydroxide solution. The amount of potassium hydroxide solution added was such as to provide the amount of KOH indicated in the examples (phr). The actual total solids content to which the suspension is diluted is chosen based on the desired phr amount of KOH and the final total solids content of the dipping composition for the latex composition. The final total solids content may be anywhere between 13% and 35%. For a final latex composition having a total solids content of about 20%, as used in these examples, the initial dilution is to about 25%-30%. The pH of the diluted suspension so produced was above 9.0, typically in the range of 9.2 to 9.6.

The diluted suspension of synthetic carboxylated polymer is placed in a mixing vessel, and the surfactant is added. The amount and identity of the surfactant was as indicated in the examples. Next the cross-linking composition added very slowly with constant stirring. The cross-linking composition is added in an amount to provide the required phr of multivalent metal to the polymer. In view of the concentrations of the streams used in the examples, the relative amounts of the two components was about 0.1 parts of cross-linking composition to 100 parts polymer suspension. This further reduces the total solids content of the polymer closer to 20%.

Next, any second cross-linking agents were added. The sequence of addition was as follows. First, any solid zinc oxide or magnesium oxide was added (if used). Second, liquid-form second crosslinking agents were added (such as glyoxal in the glyoxal examples). Third, sulphur and sulphur donors were added.

Finally, a dispersion in water of final powder materials was added. This included the titanium dioxide and antioxidant. The amount of inclusion of each is as required to provide the target formulation for the latex composition. After addition of the solid components, the pH maybe fine tuned by the addition of further alkali (the 3% KOH solution in the present examples). The total solids content of the final formulation for the latex composition for the examples was about 20%. In other cases, it may be between 5% and 40%, or between 5% and 20% for the formation of thin film articles.

3. Washing

The formers are subjected to pre-washing, to remove any remaining residues following removal of a glove previously made on the former. The formers are cleaned in mild acid/alkali and hot water. The formers are then dried by blowing air by blowers or air curtains or using ovens with the hot air having temperature above 105° C.

4. Coagulant Dipping

The cleaned dry former is immersed in a coagulant bath, which contains a 0-50% by weight solution of calcium nitrate. The coagulant also contains 0.1%-5.0% by weight metallic stearates, suitable wetting agents (0.001-1.0%) and antifoaming agents (0.001-1.0%). In some embodiments, coagulant dipping is not required. In the examples practiced here, the coagulant contained 1-13% calcium nitrate, 0.5-1.5% metallic stearate, 0.08-0.12% wetting agents and 0.005%-0.01% anti-foaming agent.

5. Drying

The coagulant coated formers are dried in a hot air circulated oven at a temperature of about 110° C. to 130° C.

6. Dipping Step

The former, coated with dried coagulant, is dipped into a tank containing the latex composition described in step 2 above. The composition is maintained at temperature of around 20-35° C., and is constantly circulated in the tank to avoid creaming and settling of the solids. The former is dipped into the composition for a dwell time of between 5 and 60 seconds. In the examples practiced here, the dwell time was 8 seconds.

7. Drying

The composition coated formers are gelled in a gelling oven at a temperature of about 100-300° C. and the duration of 2-300 seconds. In the examples practiced here, the drying conditions were 110° C. for 60 seconds.

8. Pre-Leaching

Pre-leaching is conducted by rinsing in warm water for a short period of time. The gelled film coating on the former is pre-leached in series of tanks at a temperature anywhere between ambient and 95° C. In the examples it was typically about 55° C. In the case of single dipping of elastomer, preleaching is completed as per this sequence. In case of multiple dipping of latex composition, this is completed after the final dip into the latex composition followed by gelling.

9. Second Dipping Step

The gelled elastomeric film coating on the former is dipped into a tank containing the latex composition, which contains the components specified for the given example (as prepared through step 2). The composition is maintained at temperature of around 20-40° C., and is constantly circulated in the tank to avoid creaming and settling of solids. The former is dipped into the composition for a dwell time of 5-90 seconds. In the examples practiced here, the second dip dwell time was 8 seconds.

10. Gelling/Pre Leaching/Beading

The product following the second dipping step is subjected to gelling and pre-leaching and beading. In the case of on-line polymer coating the sequence is gelling/preleaching/polymer coating/beading.

The beading, drying and pre-leaching steps can be carried out in any order. The processes of beading and pre-cure leaching could be exchange depending on the quality of cuff beading.

11. Curing

The beaded glove is then cured. Curing was conducted at about 80° C.-150° C. for about 15-30 minutes, depending upon the film thickness and intended end product physical properties.

12. Post-Leaching/Lubricant/Final Drying/Stripping/Tumbling

In the case of a glove product, the cured elastomeric article may be subjected to one or more process steps including post-leaching, chlorination (noting that this could alternatively take place before curing), neutralisation, additional curing/surface treatment and/or lubricant application (e.g. through dipping into a lubricant composition). The gloves will be stripped from the former and dried. Packaging may follow. Where additional curing or surface treatment is required, the gloves could be tumbled using hot air at a temperature around 80-120° C. for about 15-120 minutes.

Test Procedure

For all of the Examples, tests were performed to determine the following properties of the films:
Modulus at 300%
Modulus at 500%
Tensile strength (MPa/Psi) (1 MPa=145 Psi); and
Elongation %.

Tensile strength, stress at 300% and 500% modulus and elongation to break were measured by testing procedures conducted in accordance with ASTM D 412-06a (2013), based on the sample size set by the standard for gloves. The gloves were also tested for force at break measured in accordance with EN 455. The standards are readily available. These tests can be applied to multilayer films and gloves (such as examination gloves for medical applications). In all tables of results, the values indicated for the tensile strength, modulus at 300% and modulus at 500% are in units of MPa, and the elongation (or elongation at break) in %.

General Formulation Set out below is a typical formulation for the composition.

| Ingredients | Parts per Hundred Rubber (phr) - Dry basis (unless otherwise indicated) |
|---|---|
| Carboxylated synthetic polymer or blend | 100 |
| Alkali | 0.1-2.0 Sufficient to provide a pH of at least 9.0 |
| Cross-linking composition, comprising: | Added in an amount to provide the following: |
| negatively charged multivalent metal complex ions | 0.01-5.0, based on weight of metal ion per hundred parts rubber, by weight |
| alkali to solubilise and form the negatively charged multivalent metal complex ions in the cross-linking composition (providing a pH of at least 9.0 to the cross-linking composition) | 0.1-5.0 Sufficient to provide a pH of at least 9.0 |
| mechanical stabilizer for maintaining the metal complex ion in solution | 0-5.0 |
| Emulsifier stabilizers | 0.1-5.0 |
| Antiozonant | 0.0-5.0 |
| Covalent cross-linking agent | 0.0-4.0 |
| Insoluble ionic cross-linking agent | 0.0-4.0 |
| Sulphur and Sulphur donor cross-linking agents | 0.0-5.5 |
| Antioxidant | 0.2-3.0 |
| Opaqueness provider | 0.0-5.0 (when present, 0.01-5.0) |
| Pigment | As per requirement |
| Defoamer | 0.001-2.0 |

EXAMPLES

In each of the examples, other than comparative examples, a cross-linking composition was prepared from selected components of the overall formulation indicated, using step 1 of the general procedure outlined above. The cross-linking composition was combined with a commercially available carboxylated synthetic polymer (the identity of which is outlined in the examples), in accordance with steps 2 and 3 of the general procedure, in amounts to produce the latex compositions set out in the relevant table. A film was produced using the steps of the general procedure from the latex composition.

Example 1—Sodium Aluminate

Films were produced using the compositions shown below, each containing solubilised aluminium.

| | Composition in phr (parts per hundred parts of dry rubber) | | | | | | | | |
|---|---|---|---|---|---|---|---|---|---|
| Experiment no. | 1-1 | 1-2 | 1-3 | 1-4 | 1-5 | 1-6 | 1-7 | 1-8 | 1-9 |
| Polymer | 100 | 100 | 100 | 100 | 100 | 100 | 100 | 100 | 100 |
| Surfactant | 0.2 | 0.2 | 0.2 | 0.2 | 0.2 | 0.2 | 0.2 | 0.2 | 0.2 |

-continued

| | Composition in phr (parts per hundred parts of dry rubber) | | | | | | | | |
|---|---|---|---|---|---|---|---|---|---|
| Experiment no. | 1-1 | 1-2 | 1-3 | 1-4 | 1-5 | 1-6 | 1-7 | 1-8 | 1-9 |
| KOH | 1.7 | 1.7 | 1.7 | 1.7 | 1.7 | 1.7 | 1.7 | 1.7 | 1.7 |
| Antioxidant | 0.4 | 0.4 | 0.4 | 0.4 | 0.4 | 0.4 | 0.4 | 0.4 | 0.4 |
| Tio2 | 3 | 3 | 3 | 3 | 3 | 3 | 3 | 3 | 3 |
| Sodium aluminate | 0.05 | 0.1 | 0.15 | 0.2 | 0.4 | 0.6 | 0.8 | 1.0 | 1.67 |
| NaOH | 0.05 | 0.1 | 0.15 | 0.2 | 0.4 | 0.6 | 0.8 | 1.0 | 1.67 |
| KOH | 0.05 | 0.1 | 0.15 | 0.2 | 0.4 | 0.6 | 0.8 | 1.0 | 1.67 |
| Glycerine | 0.05 | 0.1 | 0.15 | 0.2 | 0.4 | 0.6 | 0.8 | 1.0 | 1.67 |

Polymer=commercially available carboxylated acrylonitrile butadiene latex—Nantex 6772

Surfactant=SDBS; Antioxidant is Lowinox CPL, a hindered phenolic antioxidant.

Sodium aluminate—the phr amounts refer to the total sodium aluminate. For corresponding phr amount of aluminium ions in solubilised form, multiply by 33%.

The properties of the films produced were tested and are set out in the table below:

| | | Consolidated Results of Physical Properties | | | | | | |
|---|---|---|---|---|---|---|---|---|
| | | Unaged | | | | Accelerated Aging (100 deg. C./22 hrs) | | |
| Expt. | MMO (phr) | Tensile (Mpa) | EB % | M300 (Mpa) | M500 (Mpa) | Tensile (Mpa) | EB % | M300 (Mpa) | M500 (Mpa) |
| 1-1 | 0.05 | 17.96 | 790 | 1.58 | 2.86 | 21.90 | 760 | 1.68 | 3.09 |
| 1-2 | 0.1 | 23.50 | 800 | 1.99 | 3.70 | 27.71 | 730 | 2.14 | 4.47 |
| 1-3 | 0.15 | 30.83 | 700 | 3.55 | 7.10 | 35.08 | 650 | 4.58 | 9.82 |
| 1-4 | 0.2 | 30.50 | 740 | 2.71 | 5.79 | 31.41 | 660 | 2.73 | 7.09 |
| 1-5 | 0.4 | 31.54 | 660 | 4.06 | 10.42 | 36.07 | 620 | 4.15 | 12.78 |
| 1-6 | 0.6 | 28.97 | 540 | 6.18 | 22.53 | 37.55 | 550 | 9.31 | 30.55 |
| 1-7 | 0.8 | 31.40 | 610 | 4.49 | 15.93 | 40.41 | 580 | 6.65 | 21.68 |
| 1-8 | 1 | 33.48 | 590 | 5.48 | 17.56 | 43.19 | 550 | 9.98 | 32.99 |
| 1-9 | 1.67 | 31.64 | 540 | 8.19 | 23.65 | 35.57 | 560 | 10.35 | 30.06 |

Analysis of Results:

The use of solubilised sodium aluminate (providing an aqueous solution of negatively charged aluminium hydroxide complex ions), as the sole cross-linking agent, provides articles such as films with good physical properties, even at lower phr levels.

The before aging tensile strength values were between 18 MPa and 33.5 MPa, and the after aging tensile strength values were between 22 MPa and 43 MPa, with the increasing level of sodium aluminate, showing the relationship of direct proportionality to the quantity of sodium aluminate. Considering the ASTM Standard Specification for Nitrile rubber examination gloves (ASTM D6319) minimum requirement of 14 MPa for examination gloves, the glove will pass the strength criteria comfortably even with the sodium aluminate level of less than 0.1 phr.

The above trend applies to M300 and M500 values too. At the lowest level of 0.05 sodium aluminate the M300 is less than 2 MPa and M300 is less than 3 MPa. This indicates the gloves softness is close to the gloves made out of natural rubber latex.

The before aging elongation at break is between 800% and 540% at unaged condition and between 760% and 550% in the accelerated aging condition at 100° C., for 22 hrs. Against the ASTM Standard Specification for Nitrile rubber examination gloves (ASTM D6319) minimum requirement of 500% unaged and 400% after accelerated aging, the gloves of Example 1 surpass the requirements.

The above results imply the following:

a. The crosslinking density increases with the increasing dosage of solubilised negatively-charged multivalent metal complex ions, even though it is not truly linear, and the slope of the curve varies when compared between tensile strength and elongation. In the case of unaged tensile strength, the increase is not so significant after 0.15 phr—this could be due to the limitation of available carboxylic group (—COOH).

b. The fact that such a high tensile could be achieved even with 0.15 phr indicates that effective dissolution/ionization of the multivalent metal (as a negatively-charged metal complex ion) enables best reaction potential. Moreover, for trivalent metals such as aluminium, the theoretical possibility of cross linking is 50% more than that of divalent metal ions. This makes a substantial impact. At lower level of multivalent metal the linear linkages are predominant and hence the elongation is high and modulus is low. At the higher level of multivalent metal, particularly a trivalent metal, the cross linking between the linear chains are more and there is a higher occurrence of three dimensional cross linking resulting in lower elongation and higher modulus, although with a marginal loss of the soft elastomeric state as a consequence of the higher cross linking density. Of course, this entire networking depends on the available carboxylic acid terminals and the number of active ions.

c. This is achieved with lower cost, particularly in the example of sodium aluminate as the source for the negatively charged multivalent metal complex ions. The cost of sodium aluminate is around one third that of solid-state ZnO. Together with the potential to use sodium aluminate at a much lower dosage (by total weight of material, based on typical ZnO usage levels), savings may be 10 to 20 fold.

d. At lower level of cross-linking agent (the multivalent metal in complex ion form), the modulus at 300% is almost the same as natural rubber, which imparts softness to the film even at low film thickness, or low film weight (e.g. for a glove having a weight of less than 4 gms (3.2 gm)). Such a low product weight will be possible with reasonable product endurance of 1-4 hrs of normal wearing conditions.

Through the use of a solubilised form of multivalent metal (i.e. through the formation of negatively charged complex of the multivalent metal), it is believed that the multivalent metal forms cross-links with carboxyl groups of the carboxylated polymer during the crosslinking or curing stage in the manufacture of the article.

Comparative Example 2—Glyoxal or TMPTMA as the Sole Cross-Linking Agent

This comparative example was performed to evaluate films produced with alternative cross-linking agents of either the organic or inorganic type. Films were produced using the compositions shown below, which contained glyoxal or trimethylolpropane trimethacrylate multifunctional methacrylate polymer (TMPTMA) as the cross-linking agent, in place of the solubilised sodium aluminate. These films were produced in accordance with steps 4-12 of the general procedure outlined above, following production of the latex composition in accordance with prior art practices.

| | Composition in phr (parts per hundred parts of dry rubber) | | | | | |
|---|---|---|---|---|---|---|
| Experiment no. | 2-1 | 2-2 | 2-3 | 2-4 | 2-5 | 2-6 |
| Polymer | 100 | 100 | 100 | 100 | 100 | 100 |
| Surfactant | 0.6 | 0.6 | 0.6 | 0.6 | 0.6 | 0.6 |
| KOH | 1.7 | 1.7 | 1.7 | 1.7 | 1.7 | 1.7 |
| Antioxidant | — | — | — | — | — | — |
| TiO2 | 3 | 3 | 3 | 3 | 3 | 3 |
| Glyoxal | 0.5 | 1.0 | 1.5 | — | — | — |
| TMPTMA | — | — | — | 0.5 | 0.1 | 1.5 |

Polymer=commercially available carboxylated acrylonitrile butadiene latex—Nantex 6772

Surfactant=50% SDBS and 50% SLES; Antioxidant is Lowinox CPL, a hindered phenolic antioxidant.

Sodium aluminate—the phr amounts refer to the total sodium aluminate. For corresponding phr amount of aluminium ions in solubilised form, multiply by 33%.

The properties of the films produced were tested and are set out in the table below:

| | | Consolidated Results | | | | | | |
|---|---|---|---|---|---|---|---|---|
| | Glyoxal | Unaged | | | | Aged - at 100 deg. C./22 hrs | | |
| Expt. | (phr) | Tensile | EB | M300 | M500 | Tensile | EB | M300 | M500 |
| 2-1 | 0.5 | 1.61 | 940 | 0.66 | 0.68 | 5.41 | 860 | 0.97 | 1.15 |
| 2-2 | 1.0 | 6.73 | 940 | 0.98 | 1.32 | 9.88 | 850 | 1.08 | 1.68 |
| 2-3 | 1.5 | 10.57 | 750 | 1.49 | 2.42 | 11.96 | 730 | 1.57 | 2.56 |

| | | Consolidated Results | | | | | | |
|---|---|---|---|---|---|---|---|---|
| | TMPTMA | Unaged | | | | Aged - at 100 deg. C./22 hrs | | |
| Expt. | (phr) | Tensile | EB | M300 | M500 | Tensile | EB | M300 | M500 |
| 2-4 | 0.5 | 9.4 | 780 | 1.3 | 2.1 | 18.7 | 760 | 1.6 | 2.9 |
| 2-5 | 1.0 | 12.7 | 780 | 1.4 | 2.4 | 16.9 | 740 | 1.8 | 3.3 |
| 2-6 | 1.5 | 8.2 | 780 | 1.1 | 1.8 | 15.5 | 740 | 1.5 | 2.8 |

Analysis of the Results:

These results assist to demonstrate the film properties as a baseline, so that combinations of other cross-linking agents with glyoxal or TMPTMA can be assessed. Glyoxal reacts with hydroxyl groups and form links however not as strongly as the ionic bonds created with multivalent metals, thus leading to poor film formation. TMPTMA is a tri functional reactive methacrylate monomer rendering covalent bond with the base polymer.

Example 3—Combinations of Sodium Aluminate with Glyoxal or TMPTMA

This example was performed to evaluate the film behaviour using solubilised sodium aluminate together with an organic cross linker, providing covalent cross-linking. These films were produced in accordance with the general procedure outlined above.

| | Composition in phr (parts per hundred parts of dry rubber) | | | |
|---|---|---|---|---|
| Experiment no. | 3-1 | 3-2 | 3-3 | 3-4 |
| Polymer | 100 | 100 | 100 | 100 |
| Surfactant | 1.0 | 1.0 | 1.0 | 1.0 |
| KOH | 1.8 | 1.8 | 1.8 | 1.8 |
| Antioxidant | 0.5 | 0.5 | 0.5 | 0.5 |
| TiO2 | 3 | 3 | 3 | 3 |
| Sodium aluminate | 0.1 | 0.1 | 0.2 | 0.2 |
| NaOH | 0.1 | 0.1 | 0.2 | 0.2 |
| KOH | 0.1 | 0.1 | 0.2 | 0.2 |
| Glycerine | 0.1 | 0.1 | 0.2 | 0.2 |
| Glyoxal | 0.5 | 1.0 | 1.5 | 2.0 |
| TMPTMA | 0.5 | 1.0 | 1.5 | 2.0 |

Polymer=commercially available carboxylated acrylonitrile butadiene latex—Nantex 6772

Surfactant=50% SDBS and 50% SLES; Antioxidant is Lowinox CPL, a hindered phenolic antioxidant.

Sodium aluminate—the phr amounts refer to the total sodium aluminate. For corresponding phr amount of aluminium ions in solubilised form, multiply by 33%.

The properties of the films produced were tested and are set out in the table below:

| Consolidated Results | | | | | | | |
|---|---|---|---|---|---|---|---|
| | Unaged | | | | Aged - at 100 deg. C./22 hrs | | |
| Expt. | Tensile | EB | M300 | M500 | Tensile | EB | M300 | M500 |
| 3-1 (0.1, 0.5, 0.5) | 15.4 | 777 | 1.4 | 2.5 | 17.7 | 715 | 1.8 | 3.7 |
| 3-2 (0.1, 1, 1) | 19.9 | 767 | 1.8 | 3.4 | 25.8 | 720 | 2.1 | 4.5 |
| 3-3 (0.2, 1.5, 1.5) | 23.6 | 720 | 2.2 | 4.9 | 30.9 | 693 | 2.7 | 6.6 |
| 3-4 (0.2, 2, 2) | 21.0 | 740 | 2.1 | 4.6 | 27.8 | 720 | 2.4 | 5.7 |

Analysis of the Results:

Following completion of Example 1, it was postulated that the addition of an organic cross-linking agent would improve the film properties. It was postulated that an organic cross linker would provide covalent bonds which would improve the elastic properties and water resistance properties of the film. The covalent bond acts like a micro spring to enable comparably better elasticity and sustaining of the same.

This example involved the preparation of four sets of experiments: two containing 0.1 phr of sodium aluminate, and two containing 0.2 phr sodium aluminate. Comparing the results obtained to those in Example 1, the following observations were made:

a. In Example 1, it was observed that increasing the amount of sodium aluminate (i.e. the amount of solubilised aluminium) increases the tensile strength and the modulus and reduces the elongation.

b. The additional inclusion of an organic cross linker in this zone of 0.1 phr sodium aluminate does not significantly change the film properties obtained—this may be attributed to insufficient ionic bonding. Another possible explanation is that the film formation starves the opportunity to obtain optimal completion of ionic bonding.

c. As seen in Example 1, where only sodium aluminate is used as the cross-linking agent, an optimum reached between 0.15 to 0.2 phr of sodium aluminate (noting that this corresponds to about 0.05-0.67 phr aluminium ions). As a consequence, experiments 3-3 and 3-4 were selected at the sodium aluminate level of 0.2 phr.

d. For 3-3 and 3-4, which are based on the same amount of sodium aluminate, the increase in the amount of organic cross-linker in the formulation reduces the modulus and increases the elongation. The gloves too felt relatively soft and silky touch—perceived to be less creased.

e. Comparing Example 3-4 to Example 1-4, each of which contains the same amount of sodium aluminate, there is a reduction in the Modulus at 300% and 500% from 2.71 to 2.1 and 5.79 to 4.6 respectively. In the case of an aged sample, the M300% and M500% drops are from 2.73 to 2.4 and 7.1 to 5.7 respectively. This supports the inference in point d.

f. Further to the above point, the unaged modulus remains the same, however the aged elongation at break increases when adding the organic cross-linker (i.e. comparing 3-4 to Example 1-4), from 660% to 720%.

Example 4—Combination of Sodium Aluminate with a Sulphur-Based Cross-Linker

This example was performed to understand the influence of sulphur and sulphur-donor cross-linkers on films also containing solubilised sodium aluminate. Three different sulphur donors were selected—ZDBC, ZDMC and DPTT. These films were produced in accordance with the general procedure outlined above.

| | Composition in phr (parts per hundred parts of dry rubber) | | | | |
|---|---|---|---|---|---|
| Experiment no. | 4-1 | 4-2 | 4-3 | 4-4 | 4-5 |
| Polymer | 100 | 100 | 100 | 100 | 100 |
| SDBS Surfactant | 0.5 | 0.5 | 0.5 | 1.0 | 0.5 |
| SLES Surfactant | 0.5 | 0.5 | — | — | — |
| KOH | 1.8 | 1.7 | 1.7 | 1.8 | 1.7 |
| Antioxidant | 0.5 | 0.5 | 0.5 | 0.5 | 0.5 |
| TiO2 | 3 | 3 | 3 | 3 | — |
| Sulphur | 1 | 0.25 | 0.25 | 1 | 0.5 |
| ZDMC | — | 0.25 | — | — | — |
| DPTT | — | — | 0.25 | — | 0.5 |
| ZDBC | 0.25 | — | — | 0.2 | — |
| Sodium aluminate | 0.05 | 0.05 | 0.05 | 0.1 | 0.15 |
| NaOH | 0.05 | 0.05 | 0.05 | 0.1 | 0.15 |
| KOH | 0.05 | 0.05 | 0.05 | 0.1 | 0.15 |
| Glycerine | 0.05 | 0.05 | 0.05 | 0.1 | 0.15 |
| Glyoxal | — | 1 | 1 | 1 | 1 |

Polymer=commercially available carboxylated acrylonitrile butadiene latex—Nantex 6772 Antioxidant is Lowinox CPL, a hindered phenolic antioxidant.

The properties of the films produced were tested and are set out in the table below. For convenient comparison, parts of the table of results for Example 1 are also shown in the second table below:

| Consolidated Results | | | | | | | | |
|---|---|---|---|---|---|---|---|---|
| | Unaged | | | | Aged - at 100 deg. C./22 hrs | | | |
| Expt. | Tensile | EB | M300 | M500 | Tensile | EB | M300 | M500 |
| 4-1 | 23.61 | 740 | 2 | 4.16 | 26.23 | 680 | 2.37 | 5.65 |
| 4-2 | 17.09 | 730 | 1.81 | 3.51 | 17.69 | 680 | 1.96 | 4.27 |
| 4-3 | 12.88 | 790 | 1.35 | 2.27 | 13.60 | 780 | 1.54 | 2.67 |
| 4-4 | 16.41 | 740 | 1.35 | 2.30 | 17.69 | 730 | 1.81 | 3.61 |
| 4-5 | 19.53 | 730 | 1.71 | 3.44 | 30.97 | 720 | 2.36 | 5.95 |

| Results From | Sodium aluminate | Unaged | | | | Aged | | | |
|---|---|---|---|---|---|---|---|---|---|
| Expt. 1 | Level | Tensile | EB | M300 | M500 | Tensile | EB | M300 | M500 |
| 1-1 | 0.05 | 17.96 | 790 | 1.58 | 2.86 | 21.90 | 760 | 1.68 | 3.09 |
| 1-2 | 0.10 | 23.50 | 800 | 1.99 | 3.70 | 27.71 | 730 | 2.14 | 4.47 |
| 1-3 | 0.15 | 30.83 | 700 | 3.55 | 7.10 | 35.08 | 650 | 4.58 | 9.82 |

Tensile, M300 & M500 are in mPa; Elongation at break in percentage.

Analysis of the Results:

It is useful to compare 4-1, 4-2 and 4-3 with Example 1-1 (which contains the same level of sodium aluminate), 4-4 with Example 1-2, and 4-5 with Example 1-3.

a. In Example 1-1, the sodium aluminate amount of 0.05 phr alone provided a tensile strength of about 18 MPa. The addition of sulphur in an amount of 1 phr and ZDBC in an amount of 0.25 phr only provided an additional tensile strength of about 5 MPa—this indicates that the solubilised sodium aluminate provides the maximum strength with the minimal dosage of 0.05 phr which is equivalent to 1/25 (on a weight basis) of the combined amount of sulphur and sulphur donors.

b. On an overall basis the unaged elongation is more than 730% in all the experiments and in 4-3 it reached up to 790% (where DPTT is used).

c. In the case of after-aging elongation, the values ranges from 680% to 780% (DPTT).

d. In the case of un-aged M300 values except CS1, all the un-aged values are less than 2 MPa, which is an indication of the softness of the film.

e. In the case of aged M300 values, 4-2, 4-3 and 4-4 were found to have values less than 2 MPa.

f. In the case of un-aged M500 values, four of the readings were below 4, and two were below 3 MPa.

g. In the case of aged M500 values, three products had values less than 5, two products had values less than 4, and one product had a value less than 3.

h. When the amount of solubilised sodium aluminate at the lowest amount tested of 0.05, the higher amount of sulphur (in presence of ZDBC) increased the strength of the film.

i. As shown previously above, the optimum ionic cross linking is reached at 0.15 phr of sodium aluminate (i.e. 0.05 phr aluminium). It is useful therefore to compare the results obtained in Example 1-3 (0.15 phr sodium aluminate) and Example 4-5 (containing 0.15 phr sodium aluminate and sulphur). The modulus values of both M300 and M500 is substantially reduced by the addition of the sulphur (and DPTT) for both unaged and aged conditions. The elongation of Example 4-5 is higher than that of Example 1-3 in both unaged and aged conditions. This is desirable.

j. Similarly, the modulus values obtained in Example 4-4 are more desirable than those obtained in Example 1-2. The modulus values of both M300 and M500 substantially reduces in the case of sulphur addition, for both unaged and aged conditions.

k. Hence it can be deduced that where lower modulus values are desired, covalent bonding through sulphur and sulphur donor addition to the formulation is effective.

For gloves, the presence of both of ionic cross-links (particularly as can be achieved with the solubilised negatively-charged multivalent metal complex ion-containing cross-linking agent) and covalent crosslinking mechanism is desirable in the formation of products such as gloves.

Example 5—Other Sources of Cross-Linking Agent

Films were produced using the compositions shown below, each containing solubilised aluminium. This example was performed to demonstrate the production of films using different sources for the cross-linking agent—that is, through replacing the sodium aluminate with alum (potassium aluminium sulphate), PAC (poly aluminium chloride) and PFS (poly ferric sulphate), and to enable evaluation of the films produced. The films were produced in accordance with the general procedure outlined above, including all of steps 1 to 12.

| | Composition in phr (parts per hundred parts of dry rubber) | | | | | | | | | |
|---|---|---|---|---|---|---|---|---|---|---|
| Experiment no. | 5-1 | 5-2 | 5-3 | 5-4 | 5-5 | 5-6 | 5-7 | 5-8 | 5-9 | 5-10 |
| Polymer | 100 | 100 | 100 | 100 | 100 | 100 | 100 | 100 | 100 | 100 |
| SDBS Surfact't | 0.4 | 0.4 | 0.4 | 0.4 | 0.4 | 0.4 | 0.4 | 0.4 | 0.4 | 0.4 |
| KOH | 1.8 | 1.8 | 1.8 | 1.8 | 1.8 | 1.8 | 1.8 | 1.8 | 1.8 | 1.8 |
| Antioxidant | 0.4 | 0.4 | 0.4 | 0.4 | 0.4 | 0.4 | 0.4 | 0.4 | 0.4 | 0.4 |
| Tio2 | 3 | 3 | 3 | 3 | 3 | 3 | 3 | 3 | 3 | 3 |
| ALUM X-Link | 0.675 | 0.338 | 0.169 | 0.084 | — | — | — | — | — | — |
| PAC X-Link | — | — | — | — | 0.930 | 0.465 | 0.233 | 0.116 | — | — |
| PFS X-Link | — | — | — | — | — | — | — | — | 0.75 | 0.5 |

Polymer=commercially available carboxylated acrylonitrile butadiene latex—Nantex 6772 Antioxidant is Lowinox CPL, a hindered phenolic antioxidant.

ALUM X-Link, PAC X-Link and PFS X-Link is a shorthand reference to the compositions set out in the table that follows immediately below. The phr amounts in the above table refer to the phr amounts of the ALUM, PAC and PFS (alone). As shown in the table below, the relevant X-Linker contained additional components.

| | Cross linking composition | | | | | |
|---|---|---|---|---|---|---|
| | | Composition in phr | | | | |
| Experiment | Salt | Salt | NaOH | KOH | Glycerine | SDBS |
| 5-1 | Alum | 0.675 | 1.35 | 0.675 | 0.675 | 0.6 |
| 5-2 | Alum | 0.338 | 1.35 | 0.675 | 0.675 | 0.6 |
| 5-3 | Alum | 0.169 | 1.35 | 0.675 | 0.675 | 0.6 |
| 5-4 | Alum | 0.084 | 1.35 | 0.675 | 0.675 | 0.6 |
| 5-5 | PAC | 0.930 | 0.93 | 0.75 | 0.75 | 0.6 |
| 5-6 | PAC | 0.465 | 0.93 | 0.75 | 0.75 | 0.6 |
| 5-7 | PAC | 0.233 | 0.93 | 0.75 | 0.75 | 0.6 |
| 5-8 | PAC | 0.116 | 0.93 | 0.75 | 0.75 | 0.6 |
| 5-9 | PFS | 0.75 | 3 | 0.675 | 0.675 | 0.6 |
| 5-10 | PFS | 0.5 | 3 | 0.675 | 0.675 | 0.6 |

The properties of the films produced were tested and are set out in the table below.

| Expt | Trivalent Salt phr | UNAGED | | | | AGED | | | |
|---|---|---|---|---|---|---|---|---|---|
| | | Tensile | EB | M300 | M500 | Tensile | EB | M300 | M500 |
| Alum | | | | | | | | | |
| 5-1 | 0.675 | 27.46 | 610 | 3.51 | 10.68 | 34.02 | 700 | 3.23 | 7.02 |
| 5-2 | 0.338 | 28.45 | 610 | 3.98 | 10.7 | 32.09 | 630 | 3.41 | 9.94 |
| 5-3 | 0.169 | 31.79 | 640 | 3.16 | 8.74 | 36.79 | 650 | 3.21 | 8.05 |
| 5-4 | 0.084 | 40.38 | 640 | 3.9 | 11.86 | 37.64 | 600 | 3.96 | 16.53 |
| Poly Aluminium Chloride phr | | | | | | | | | |
| 5-5 | 0.930 | 33.78 | 620 | 3.15 | 10.29 | 38.07 | 620 | 4.01 | 13.15 |
| 5-6 | 0.465 | 34.26 | 610 | 4.31 | 13.67 | 36.32 | 630 | 3.59 | 10.3 |
| 5-7 | 0.233 | 34.23 | 620 | 3.82 | 10.76 | 22.54 | 690 | 2.28 | 4.9 |
| 5-8 | 0.116 | 32.08 | 600 | 3.93 | 12.96 | 37.77 | 620 | 4.01 | 13.52 |
| Poly Ferric Sulphate phr | | | | | | | | | |
| 5-9 | 0.75 | 31.14 | 580 | 5.17 | 19.12 | 18.7 | 640 | 2.63 | 5.75 |
| 5-10 | 0.5 | 28.36 | 600 | 3.67 | 11.73 | 36.45 | 630 | 4.03 | 12.71 |

Analysis of the Results:

The results of Example 5 demonstrate that it is possible to produce products from latex compositions containing cross-linking compositions based on sources of multivalent metals other than sodium aluminate—the salt forms in particular. Films were produced from the latex compositions containing ionic cross-linking based on the metals present in the cross-linking compositions. The alum and PAC were able to form clear solutions of the cross-linking agent. The properties of the films produced did not follow the typical pattern shown in earlier examples of increasing tensile strength with increasing cross-linking agent amounts. This suggests that the additional ions present in the compositions may be influencing the cross-linking. Further modifications to the compositions are expected to result in improvements to the films produced in these examples.

Example 6—Sodium Aluminate with Added Solid Metal Oxide Cross-Linking Agents

This example was performed to explore the properties of films containing solubilised negatively-charged aluminium hydroxide complex ions, distributed evenly throughout the product, together with traditional solid ionic cross-linking agent, which will be concentrated around the particles in the final product. These films were produced in accordance with the general procedure outlined above, with the sodium aluminate being solubilised prior to addition to the polymer suspension, and later addition of the metal oxide as one of the finely milled solid components. The input components were as outlined in the following table:

| | Composition in phr parts per hundred parts of dry rubber) | | | | | | | |
|---|---|---|---|---|---|---|---|---|
| Experiment No | 6-1 | 6-2 | 6-3 | 6-4 | 6-5 | 6-6 | 6-7 | 6-8 |
| Polymer | 100 | 100 | 100 | 100 | 100 | 100 | 100 | 100 |
| KOH | 1.7 | 1.7 | 1.7 | 1.7 | 1.7 | 1.7 | 1.7 | 1.7 |
| SDBS-Surfactant | 0.3 | 0.3 | 0.3 | 0.3 | 0.3 | 0.3 | 0.3 | 0.3 |
| SLES-Surfactant | 0.3 | 0.3 | 0.3 | 0.3 | 0.3 | 0.3 | 0.3 | 0.3 |
| Antioxidant | 0.4 | 0.4 | 0.4 | 0.4 | 0.4 | 0.4 | 0.4 | 0.4 |
| TiO2 | 3 | 3 | 3 | 3 | 3 | 3 | 3 | 3 |
| Sodium aluminate | 0.15 | 0.15 | 0.15 | 0.15 | 0.15 | 0.15 | 0.15 | 0.15 |
| NaOH | 0.15 | 0.15 | 0.15 | 0.15 | 0.15 | 0.15 | 0.15 | 0.15 |
| KOH | 0.15 | 0.15 | 0.15 | 0.15 | 0.15 | 0.15 | 0.15 | 0.15 |
| Glycerine | 0.15 | 0.15 | 0.15 | 0.15 | 0.15 | 0.15 | 0.15 | 0.15 |
| Zinc Oxide | 0.05 | 0.1 | 0.15 | 0.2 | | | | |
| Magnesium Oxide | | | | | 0.05 | 0.1 | 0.15 | 0.2 |

| | Composition in phr (parts per hundred parts of dry rubber) | | | | | |
|---|---|---|---|---|---|---|
| Experiment No | 6-9 | 6-10 | 6-11 | 6-12 | 6-13 | 6-14 |
| Polymer | 100 | 100 | 100 | 100 | 100 | 100 |
| KOH | 1.7 | 1.7 | 1.7 | 1.7 | 1.7 | 1.7 |
| SDBS-Surfactant | 0.3 | 0.3 | 0.3 | 0.3 | 0.3 | 0.3 |
| SLES-Surfactant | 0.3 | 0.3 | 0.3 | 0.3 | 0.3 | 0.3 |
| Antioxidant | 0.4 | 0.4 | 0.4 | 0.4 | 0.4 | 0.4 |
| TiO2 | 3 | 3 | 3 | 3 | 3 | 3 |
| Sodium aluminate | 0.075 | 0.075 | 0.075 | 0.075 | 0.075 | 0.075 |
| NaOH | 0.075 | 0.075 | 0.075 | 0.075 | 0.075 | 0.075 |
| KOH | 0.075 | 0.075 | 0.075 | 0.075 | 0.075 | 0.075 |
| Glycerine | 0.075 | 0.075 | 0.075 | 0.075 | 0.075 | 0.075 |
| Zinc Oxide | 0.025 | 0.05 | 0.075 | 0.1 | 0 | 0 |
| Magnesium Oxide | 0.05 | 0.025 | 0 | 0 | 0.075 | 0.1 |

Polymer=commercially available carboxylated acrylonitrile butadiene latex—Nantex 6772 Antioxidant is Lowinox CPL, a hindered phenolic antioxidant.

The properties of the films produced were tested and are set out in the table below.

| Experiment No | UNAGED | | | | AGED | | | |
|---|---|---|---|---|---|---|---|---|
| | Tensile | EB | M300 | M500 | Tensile | EB | M300 | M500 |
| 6-1 | 26.01 | 680 | 2.71 | 6.6 | 26.72 | 680 | 2.89 | 6.62 |
| 6-2 | 23.94 | 670 | 2.53 | 6.31 | 25.45 | 670 | 2.2 | 4.76 |
| 6-3 | 29.91 | 670 | 3.01 | 7.5 | 27.61 | 650 | 2.46 | 6.4 |
| 6-4 | 29.16 | 650 | 3.02 | 7.75 | 35.36 | 650 | 3.53 | 8.9 |
| 6-5 | 22.29 | 690 | 2.25 | 4.6 | 25.49 | 660 | 2.47 | 5.95 |
| 6-6 | 23.27 | 680 | 2.29 | 5.26 | 26.21 | 650 | 2.49 | 6.11 |
| 6-7 | 18.81 | 690 | 2.01 | 3.99 | 22.78 | 650 | 2.21 | 5.22 |
| 6-8 | 20.76 | 740 | 1.85 | 3.47 | 22.79 | 690 | 1.9 | 3.96 |
| 6-9 | 20.1 | 740 | 1.87 | 3.67 | 19.26 | 670 | 2.06 | 4.25 |
| 6-10 | 20.46 | 730 | 1.92 | 3.76 | 23.42 | 660 | 2.3 | 5.35 |
| 6-11 | 16.72 | 740 | 1.69 | 3.37 | 21.87 | 650 | 2.09 | 4.4 |
| 6-12 | 23.68 | 710 | 2.19 | 4.36 | 26.8 | 680 | 2.62 | 6.13 |
| 6-13 | 20.76 | 690 | 1.85 | 3.87 | 24.16 | 720 | 2.5 | 5.15 |
| 6-14 | 23.68 | 710 | 2.19 | 4.36 | 19.63 | 690 | 2.27 | 4.53 |

Analysis of Results:

The results obtained show that there is a slight improvement to the film through the addition of a second cross-linker, comprising a solid metal oxide. The film formation (uniform film formation) is good when a small quantity of ZnO or MgO is added.

Comparative Example 7—ZnO as Sole Ionic Cross-Linking Agent

This example was performed to explore the properties of films containing solid zinc oxide as the cross-linking agent, to enable a comparison to be made against a film containing solubilised metal (in the form of negatively charged aluminium hydroxide complex ions). These films were produced in accordance with the general procedure outlined above, although without the use of the cross-linking composition of the invention. Instead, the metal oxide was added at the time indicated for that component in the general procedure. The input components were as outlined in the following tables:

| | 7-1 | 7-2 | 7-3 | 7-4 | 7-5 | 7-6 | 7-7 | 7-8 | 7-9 | 7-10 | 7-11 | 7-12 |
|---|---|---|---|---|---|---|---|---|---|---|---|---|
| NBR latex | 100 | 100 | 100 | 100 | 100 | 100 | 100 | 100 | 100 | 90 | 90 | 90 |
| Chloroprene latex | — | — | — | — | — | — | — | — | — | 10 | 10 | 10 |
| KOH | 0.5 | 0.5 | — | 0.5 | 0.5 | — | 0.5 | 0.5 | — | 0.5 | 0.5 | — |
| SDBS-Surfactant | 0.3 | — | 0.5 | 0.3 | — | 0.5 | 0.3 | — | 0.5 | 0.3 | — | 0.5 |
| Solid Zinc oxide | 1.2 | 1.2 | 1.2 | 0.6 | 0.6 | 0.6 | 2 | 2 | 2 | 2.4 | 2.4 | 2.4 |
| Anti oxidant | 0.5 | 0.5 | 0.5 | 0.5 | 0.5 | 0.5 | 0.5 | 0.5 | 0.5 | 0.5 | 0.5 | 0.5 |
| Calcium carbonate | — | — | — | 5 | 5 | 5 | 5 | 5 | 5 | 5 | 5 | 5 |
| Potassium stearate | 1 | 1 | 1 | 1 | 1 | 1 | 1 | 1 | 1 | 1 | 1 | 1 |

The antioxidant was Lowinox CPL.

The properties of the films produced were tested and are set out in the tables below.

| Consolidated Results - Part 1/4 | | | | | | | | | |
|---|---|---|---|---|---|---|---|---|---|
| | 7-1 | | | 7-2 | | | 7-3 | | |
| Property | Unaged | Aged 70 deg C. 7 days | Aged 100 deg C. 1 day | Unaged | Aged 70 deg C. 7 days | Aged 100 deg C. 1 day | Unaged | Aged 70 deg C. 7 days | Aged 100 deg C. 1 day |
| Tensile (Mpa) | 15.2 | 16.7 | 18.9 | 22.2 | 24.03 | 18.8 | 15.6 | 9.45 | 15.93 |
| M300 (Mpa) | 1.6 | 1.8 | 2.3 | 2.1 | 1.89 | 1.97 | 1.7 | 1.3 | 1.69 |
| M500 (Mpa) | 2.9 | 3.6 | 4.9 | 4 | 3.68 | 4.09 | 2.8 | 1.91 | 3.02 |
| EB (%) | 727 | 700 | 660 | 727 | 733 | 687 | 753 | 753 | 707 |
| pH | | 8.7 | | | 8.9 | | | 8.2 | |

| Consolidated Results - Part 2/4 | | | | | | | | | |
|---|---|---|---|---|---|---|---|---|---|
| | 7-4 | | | 7-5 | | | 7-6 | | |
| Property | Unaged | Aged 70 deg C. 7 days | Aged 100 deg C. 1 day | Unaged | Aged 70 deg C. 7 days | Aged 100 deg C. 1 day | Unaged | Aged 70 deg C. 7 days | Aged 100 deg C. 1 day |
| Tensile (Mpa) | 21.2 | 29.5 | 30.51 | 29.7 | 34.14 | 25.25 | 23.1 | 14.07 | 20.13 |
| M300 (Mpa) | 1.9 | 2.1 | 2.9 | 2.7 | 2.54 | 2.34 | 2 | 1.5 | 2.13 |
| M500 (Mpa) | 3.4 | 4.6 | 6.8 | 5.4 | 5.23 | 4.59 | 3.6 | 2.23 | 3.74 |
| EB (%) | 753 | 720 | 667 | 707 | 727 | 707 | 753 | 767 | 713 |
| pH | | 8.7 | | | 8.8 | | | 8.1 | |

| Consolidated Results - Part 3/4 | | | | | | | | | |
|---|---|---|---|---|---|---|---|---|---|
| | 7-7 | | | 7-8 | | | 7-9 | | |
| Property | Unaged | Aged 70 deg C. 7 days | Aged 100 deg C. 1 day | Unaged | Aged 70 deg C. 7 days | Aged 100 deg C. 1 day | Unaged | Aged 70 deg C. 7 days | Aged 100 deg C. 1 day |
| Tensile (Mpa) | 31.1 | 27.2 | 43.5 | 46.7 | 44.94 | 49.99 | 30.41 | 32.35 | 36.97 |
| M300 (Mpa) | 5.3 | 2.9 | 6.2 | 8 | 6.75 | 6.76 | 5 | 4.13 | 5.51 |
| M500 (Mpa) | 16.6 | 6.4 | 19.4 | 30 | 22.48 | 25.36 | 17.6 | 12.73 | 19.78 |
| EB (%) | 593 | 687 | 620 | 560 | 607 | 600 | 567 | 613 | 580 |
| pH | | 8.7 | | | 8.8 | | | 8.2 | |

| | Consolidated Results - Part 4/4 | | | | | | | | |
|---|---|---|---|---|---|---|---|---|---|
| | 7-10 | | | 7-11 | | | 7-12 | | |
| Property | Unaged | Aged 70 deg C. 7 days | Aged 100 deg C. 1 day | Unaged | Aged 70 deg C. 7 days | Aged 100 deg C. 1 day | Unaged | Aged 70 deg C. 7 days | Aged 100 deg C. 1 day |
| UTS (Mpa) | 27.2 | 38.6 | 38.3 | 34.2 | 38.05 | 39.07 | 35.95 | 39.11 | 37.47 |
| M300 (Mpa) | 5.4 | 6.1 | 5.9 | 7.9 | 5.39 | 5.87 | 7.7 | 4.97 | 5.36 |
| M500 (Mpa) | 16.2 | 21.4 | 17.1 | 24.9 | 15.93 | 17.51 | 24.7 | 16.42 | 18.35 |
| EB (%) | 580 | 587 | 633 | 553 | 627 | 620 | 540 | 613 | 607 |
| pH | | 9.1 | | | 9.4 | | | 8.6 | |

As stated above, examples 7-1 to 7-12 represent the use of the conventional solid zinc oxide cross-linker. The examples were performed without sulphur or other covalent cross-linking agent. The amount of ZnO used in the examples was between 0.6 and 2.4. The elongation and modulus values obtained from testing the products of this example were inferior to those of Example 1, and were reflected in poor user comfort levels.

Example 8—Double-Layer Gloves Formed Using Sodium Aluminate, Sulphur and a Sulphur Donor as the Sole Cross-Linking Agents, in Each Layer This example was performed to demonstrate commercial scale production of gloves (in different sizes) containing solubilised sodium aluminate cross-linker, together with sulphur and sulphur-donor cross-linkers as secondary cross-linkers. These films were produced in accordance with the general procedure outlined above, with the modification that the second dipping step was based on a different composition compared to the first dipping composition. The gloves were double tone (blue and white), 300 mm long, and had an average weight (for medium size) of 9.5 grams.

The composition for the 1$^{st}$ layer—the working side, was as follows (in phr):

| White Compound | |
|---|---|
| Nantex 6772 | 100 |
| KOH | 1.0 |
| Sodium aluminate | 0.1 |
| SULPHUR | 0.6 |
| ZDBC | 0.4 |
| ANTIOXIDANT | 0.4 |
| TiO$_2$ | 6.0 |
| Calcium Carbonate | 2.0 |

The composition for the 2$^{nd}$ layer—the donning side, was as follows (in phr):

| Cobalt Blue Compound | |
|---|---|
| Nantex 6772 | 100 |
| KOH | 1.0 |
| sodium aluminate | 0.1 |
| SULPHUR | 0.6 |
| ZDBC | 0.4 |
| ANTIOXIDANT | 0.4 |
| TiO$_2$ | 6.0 |

-continued

| Cobalt Blue Compound | |
|---|---|
| VIOLET BLUE | 0.5 |
| MPL1566 | 0.14 |
| MPL1857 B | 0.7 |

A) Dimensions and Physical Properties:

| | | DIMENSION | | | | | |
|---|---|---|---|---|---|---|---|
| Size | | | | | Thickness | | |
| (and sample number) | Weight (gram) | Length (mm) | Width (mm) | Cuff | Palm (mm) | Finger |
| M 8.1 | 9.56 | 301 | 97 | 0.12 | 0.13 | 0.18 |
| 8.2 | 9.44 | 304 | 99 | 0.11 | 0.14 | 0.17 |
| 8.3 | 9.72 | 304 | 99 | 0.12 | 0.14 | 0.18 |
| 8.4 | 9.83 | 302 | 99 | 0.13 | 0.14 | 0.17 |
| 8.5 | 9.63 | 302 | 99 | 0.13 | 0.14 | 0.17 |
| 8.6 | 9.72 | 301 | 99 | 0.13 | 0.14 | 0.16 |
| 8.7 | 9.46 | 301 | 98 | 0.13 | 0.14 | 0.20 |
| 8.8 | 9.89 | 302 | 99 | 0.15 | 0.13 | 0.17 |
| 8.9 | 9.56 | 300 | 99 | 0.12 | 0.13 | 0.17 |
| 8.10 | 9.74 | 301 | 99 | 0.13 | 0.14 | 0.17 |
| Average | 9.66 | 302 | 99 | 0.13 | 0.14 | 0.17 |

| | | PHYSICAL PROPERTIES UNAGED | | | | |
|---|---|---|---|---|---|---|
| Size (and sample number) | Tensile (Mpa) | Elongation (%) | Mod@300 (Mpa) | Mod@500 (Mpa) | Load Break (N) |
| M 8.1 | 16.55 | 780 | 1.77 | 2.91 | 10.78 |
| 8.2 | 18.13 | 760 | 1.86 | 3.32 | 10.50 |
| 8.3 | 17.54 | 760 | 1.80 | 3.12 | 10.56 |
| 8.4 | 18.51 | 760 | 1.90 | 3.33 | 10.23 |
| 8.5 | 17.87 | 780 | 1.73 | 2.92 | 10.47 |
| 8.6 | 17.90 | 760 | 1.82 | 3.29 | 11.10 |
| 8.7 | | | | | |
| 8.8 | | | | | |
| 8.9 | | | | | |
| 8.10 | | | | | |
| Average | 17.75 | 767 | 1.81 | 3.15 | 10.53 |

| Size (and sample number) | PHYSICAL PROPERTIES AGED | | | | |
|---|---|---|---|---|---|
| | Tensile (Mpa) | Elongation (%) | Mod@300 (Mpa) | Mod@500 (Mpa) | Load Break (N) |
| M 8.1 | 24.92 | 740 | 2.32 | 4.56 | 12.83 |
| 8.2 | 19.99 | 720 | 2.25 | 4.20 | 10.40 |
| 8.3 | 27.92 | 740 | 2.47 | 4.57 | 12.79 |
| 8.4 | 25.02 | 740 | 2.41 | 4.77 | 12.26 |
| 8.5 | 20.84 | 720 | 2.42 | 4.72 | 12.56 |
| 8.6 | 24.80 | 760 | 2.24 | 4.33 | 12.02 |
| 8.7 | | | | | |
| 8.8 | | | | | |
| 8.9 | | | | | |
| 8.10 | | | | | |
| Average | 23.92 | 737 | 2.35 | 4.53 | 12.41 |

| Size (and sample number) | DIMENSION | | | Thickness | | |
|---|---|---|---|---|---|---|
| | Weight (gram) | Length (mm) | Width (mm) | Cuff (mm) | Palm (mm) | Finger (mm) |
| L 8.1 | 10.76 | 305 | 109 | 0.11 | 0.14 | 0.16 |
| 8.2 | 10.76 | 302 | 110 | 0.11 | 0.13 | 0.18 |
| 8.3 | 10.76 | 304 | 110 | 0.12 | 0.14 | 0.18 |
| 8.4 | 11.00 | 301 | 110 | 0.13 | 0.13 | 0.16 |
| 8.5 | 11.11 | 302 | 111 | 0.13 | 0.14 | 0.19 |
| 8.6 | 10.26 | 302 | 109 | 0.11 | 0.13 | 0.16 |
| 8.7 | 10.48 | 303 | 110 | 0.11 | 0.13 | 0.16 |
| 8.8 | 10.17 | 302 | 109 | 0.11 | 0.12 | 0.16 |
| 8.9 | 9.80 | 300 | 110 | 0.11 | 0.13 | 0.17 |
| 8.10 | 10.68 | 303 | 110 | 0.11 | 0.13 | 0.18 |
| Average | 10.58 | 302 | 110 | 0.12 | 0.13 | 0.17 |

| Size (and sample number) | PHYSICAL PROPERTIES UNAGED | | | | |
|---|---|---|---|---|---|
| | Tensile (Mpa) | Elongation (%) | Mod@300 (Mpa) | Mod@500 (Mpa) | Load Break (N) |
| L 8.1 | 17.72 | 800.00 | 1.60 | 2.70 | 10.50 |
| 8.2 | 21.02 | 820.00 | 1.72 | 2.86 | 10.15 |
| 8.3 | 19.10 | 800.00 | 1.55 | 2.72 | 11.10 |
| 8.4 | 20.97 | 820.00 | 1.81 | 3.00 | 9.65 |
| 8.5 | 20.32 | 800.00 | 1.78 | 3.06 | 8.92 |
| 8.6 | 20.90 | 800.00 | 1.85 | 3.12 | 9.92 |
| 8.7 | | | | | |
| 8.8 | | | | | |
| 8.9 | | | | | |
| 8.10 | | | | | |
| Average | 20.01 | 807 | 1.72 | 2.91 | 10.04 |

| Size (and sample number) | DIMENSION | | | Thickness | | |
|---|---|---|---|---|---|---|
| | Weight (gram) | Length (mm) | Width (mm) | Cuff (mm) | Palm (mm) | Finger (mm) |
| XL 8.1 | 11.29 | 307 | 119 | 0.11 | 0.13 | 0.16 |
| 8.2 | 11.89 | 303 | 120 | 0.12 | 0.14 | 0.19 |
| 8.3 | 11.85 | 300 | 119 | 0.12 | 0.13 | 0.19 |
| 8.4 | 11.71 | 302 | 120 | 0.13 | 0.14 | 0.16 |
| 8.5 | 11.87 | 302 | 119 | 0.13 | 0.14 | 0.18 |
| 8.6 | 11.97 | 303 | 120 | 0.13 | 0.14 | 0.18 |
| 8.7 | 11.69 | 301 | 119 | 0.12 | 0.14 | 0.17 |
| 8.8 | 11.48 | 301 | 120 | 0.12 | 0.13 | 0.18 |
| 8.9 | 11.89 | 301 | 119 | 0.12 | 0.14 | 0.19 |
| 8.10 | 11.58 | 300 | 120 | 0.13 | 0.14 | 0.17 |
| Average | 11.72 | 302 | 120 | 0.12 | 0.14 | 0.18 |

| Size (and sample number) | PHYSICAL PROPERTIES UNAGED | | | | |
|---|---|---|---|---|---|
| | Tensile (Mpa) | Elongation (%) | Mod@300 (Mpa) | Mod@500 (Mpa) | Load Break (N) |
| XL 8.1 | 17.19 | 800.00 | 1.58 | 2.58 | 10.50 |
| 8.2 | 20.01 | 800.00 | 1.85 | 3.09 | 10.01 |
| 8.3 | 18.93 | 780.00 | 1.78 | 3.03 | 12.12 |
| 8.4 | 18.99 | 800.00 | 1.69 | 2.91 | 9.94 |
| 8.5 | 18.56 | 780.00 | 1.89 | 3.27 | 10.87 |
| 8.6 | 17.92 | 780.00 | 1.65 | 2.77 | 9.38 |
| 8.7 | | | | | |
| 8.8 | | | | | |
| 8.9 | | | | | |
| 8.10 | | | | | |
| Average | 18.60 | 790.00 | 1.74 | 2.94 | 10.47 |

B) Overall Physical Properties for M size

| PHYSICAL PROPERTIES UNAGED | | | | |
|---|---|---|---|---|
| Tensile (Mpa) | Elongation (%) | Mod@300 (Mpa) | Mod@500 (Mpa) | Load Break (N) |
| 20.46 | 760 | 2.04 | 3.59 | 9.55 |
| 19.96 | 760 | 1.86 | 3.28 | 9.81 |
| 20.21 | 760 | 1.95 | 3.44 | 9.68 |

| PHYSICAL PROPERTIES AGED | | | | |
|---|---|---|---|---|
| Tensile (Mpa) | Elongation (%) | Mod@300 (Mpa) | Mod@500 (Mpa) | Load Break (N) |
| 25.30 | 740 | 2.30 | 4.74 | 13.94 |
| 25.66 | 720 | 2.47 | 5.11 | 10.71 |
| 25.48 | 730 | 2.39 | 4.93 | 12.33 |

Example 9—Second Cross-Linking Agent Comprising Sulphur and Sulphur Donor

This example demonstrates the results obtained when using sulphur and sulphur-donor cross-linkers as the second cross-linking agents (the only secondary cross-linking agents) in addition to sodium aluminate as the primary cross-linking agent. These films were produced in accordance with the general procedure outlined above. The films produced were in the form of gloves with an average thickness of about 0.05-0.10 mm—less than 0.2 mm.

|  | Composition in phr | |
|---|---|---|
|  | Example 9-1 | Example 9-2 |
| Nantex 6772 | 100 | 100 |
| KOH | 1 | 1 |
| Surfactant - Agwet | 0.6 | 0.6 |
| Sodium Aluminate | 0.08 | 0.12 |
| NaOH | 0.08 | 0.12 |
| KOH | 0.08 | 0.12 |
| Glycerine | 0.08 | 0.12 |
| Sulphur | 0.6 | — |
| DPTT | 0.2 | 0.3 |
| ZDBC | 0.2 | 0.3 |
| TiO2 | 2.5 | 2.5 |
| Antioxidant | 0.4 | 0.4 |

Agwet is a sodium salt of dodecyl benzene sulfonate.

The antioxidant is Lowinox CPL, a hindered phenolic antioxidant.

The properties of the films produced were tested and are set out in the table below. It is noted that EN refers to Force at Break measured in accordance with the European Norms—the European standard EN 455-2, and is measured in Newtons.

|  |  | UNAGED | | | | |
|---|---|---|---|---|---|---|
| Compound | Weight (gm) | Tensile (Mpa) | EB (%) | M300 (Mpa) | M500 (Mpa) | EN (N) |
| Ex. 9-1 | 4.3 | 14.77 | 820 | 1.42 | 2.2 | 4.8 |
| Ex. 9-2 | 4.2 | 17.92 | 760 | 1.61 | 2.79 | 5.35 |

|  |  | AGED (100 deg. C./22 hrs) | | | | |
|---|---|---|---|---|---|---|
| Compound | Weight | Tensile | EB | M300 | M500 | EN (N) |
| Ex. 9-1 | 4.3 | 20.94 | 740 | 1.98 | 3.59 | 6.63 |
| Ex. 9-2 | 4.2 | 24.91 | 750 | 2.22 | 4.12 | 7.59 |

Analysis of the Results:

The results of Example 9 demonstrate the production of articles (gloves) having excellent properties, produced using sodium aluminate in an amount of well below 0.3 phr, in combination with either sulphur and sulphur-donor cross-linking agents, or sulphur-donor cross-linking agents without sulphur, to the exclusion of any other cross-linking agents. Comparing Example 9-1 to Example 9-2, the lower level of sodium aluminate results in lower tensile strength and higher elongation (see Example 9-1). The converse (Example 9-2) results in higher tensile strength and lower elongation. The M500 values are less than 3 before aging and less than 5 after accelerated aging—both well below 6.5, for a glove thickness of less than 0.2 mm. The product produced with sulphur and/or a sulphur donor can achieve engloation higher than 800% prior to aging, and still as high as 750% after aging. Comparing the results in Example 9 to those of Example 4, Examples 4-2 to 4-5 contain glyoxal as an additional cross-linker. Example 9-1 contains no glyoxal and contains sulphur and a sulphur donor, and Example 9-2 contains just a sulphur donor (without sulphur), in addition to the solubilised sodium aluminate cross-linking agent. In Example 9, high elongation, above 700%, is achieved with the selected cross-linking agents.

Example 10—Second Cross-Linking Agent Comprising Metal Oxide as the Sole Secondary Cross-Linking Agent This example demonstrates the results obtained when using (solid) metal oxide cross-linking agent(s) as the second cross-linking agent(s) (i.e. the only secondary cross-linking agents) in addition to sodium aluminate as the primary cross-linking agent. These films were produced in accordance with the general procedure outlined above. The films produced were in the form of gloves with an average thickness of about 0.05-0.10 mm—less than 0.2 mm.

|  | Components in phr | |
|---|---|---|
|  | Ex. 10-1 | Ex. 10-2 |
| Nantex 6772 | 100 | 100 |
| KOH | 1 | 1 |
| Surfactant - Agwet | 0.6 | 0.6 |
| Sodium Aluminate | 0.1 | 0.05 |
| NaOH | 0.1 | 0.05 |
| KOH | 0.1 | 0.05 |
| Glycerine | 0.1 | 0.05 |
| Zink Oxide | 0.2 | 0.2 |
| Magnesium Oxide | — | 0.3 |
| TiO2 | 2.5 | 2.5 |
| Antioxidant | 0.4 | 0.4 |

Agwet is a sodium salt of dodecyl benzene sulfonate.

The antioxidant is Lowinox CPL, a hindered phenolic antioxidant.

The properties of the films produced were tested and are set out in the table below. The units of measurement are the same as presented in the tables for Example 9.

|  |  | UNAGED | | | |
|---|---|---|---|---|---|
| Compound | Weight | Tensile | EB | M300 | M500 | EN |
| Ex. 10-1 | 4.2 | 22.96 | 760 | 2.03 | 3.98 | 5.4 |
| Ex. 10-2 | 4.2 | 18.41 | 740 | 1.8 | 3.27 | 6.39 |

|  |  | AGED (100 deg. C./22 hrs) | | | |
|---|---|---|---|---|---|
| Compound | Weight | Tensile | EB | M300 | M500 | EN |
| Ex. 10-1 | 4.2 | 24.07 | 720 | 2.23 | 4.34 | 6.3 |
| Ex. 10-2 | 4.2 | 21.94 | 720 | 2.11 | 3.93 | 7.41 |

Analysis of the Results:

The results of Example 10 demonstrate the production of articles (gloves) having excellent properties, produced using sodium aluminate in an amount of well below 0.3 phr, in combination with either zinc oxide or a combination of metal oxides (zinc and magnesium oxide), to the exclusion of any other cross-linking agents. Comparing Example 10-1 to Example 10-2, there is a reduction in the amount of sodium aluminate by 0.05 phr, which is substituted with 0.3 phr magnesium oxide. Even with an addition of 0.3 phr of MgO, this could not compensate for the reduction in 0.05 phr amount of sodium aluminate, in solubilised form, demonstrating again the unexpectedly high effectiveness of this reagent on a weight-for-weight basis with other possible cross-linking agents, especially considering the comparison in the tensile values obtained, where the MgO in product of Example 10-2 failed to fully compensate for the reduction in sodium aluminate. The lower level of sodium aluminate in Example 10-2 results in lower tensile and higher elongation compared to the results in Example 10-1. The M500 results are less than 4.0 before aging and less than 5.0 after aging, and well below 6.5 in each case. The elongation is at least 720% in both the aged and unaged condition, and higher than 750 in one case in the unaged condition.

The results of Example 10 provide an improvement upon the results shown in Example 6, and guide the selection of components suitable for commercial production of gloves based on a combination of solubilised sodium aluminate and metal oxide. The amounts selected follow extensive testing and optimisation, with a focus on amounts of around 0.01-0.6 phr (suitably 0.01-0.4 phr) metal oxide, and 0.01-0.2 phr sodium aluminate. Example 10-1 is preferred over Example 10-2.

Example 11—Second Cross-Linking Agent Comprising Sulphur, One or More Sulphur Donors, and One or More Metal Oxides as the Only Secondary Cross-Linking Agents This example demonstrates the results obtained when using sulphur, sulphur donor(s) and metal cross-linking agent(s) as the second cross-linking agent(s) (i.e. the only secondary cross-linking agents) in addition to sodium aluminate (or other dissolved multivalent metal oxide, hydroxide or salt) as the primary cross-linking agent. These films were produced in accordance with the general procedure outlined above. The films produced were in the form of gloves with an average thickness of about 0.05-0.10 mm—less than 0.2 mm.

|  | Components in phr | |
|---|---|---|
|  | Ex. 11-1 | Ex 11-2 |
| Nantex 6772 | 100 | 100 |
| KOH | 1 | 1 |
| Surfactant - Agwet | 0.6 | 0.6 |
| Sodium Aluminate | 0.08 | 0.1 |
| NaOH | 0.08 | 0.1 |
| KOH | 0.08 | 0.1 |
| Glycerine | 0.08 | 0.1 |
| Sulphur | 0.3 | 0.2 |
| DPTT | 0.1 | 0.1 |
| ZDBC | 0.1 | 0.05 |
| Zinc Oxide | 0.1 | 0.1 |
| Magnesium Oxide | 0.2 | 0.3 |
| TiO2 | 2.5 | 2.5 |
| Antioxidant | 0.4 | 0.4 |

Agwet is a sodium salt of dodecyl benzene sulfonate.

The antioxidant is Lowinox CPL, a hindered phenolic antioxidant.

The properties of the films produced were tested and are set out in the table below. The units of measurement are the same as presented in the tables for Example 9.

| | | UNAGED | | | | |
|---|---|---|---|---|---|---|
| Compound | Weight | Tensile | EB | M300 | M500 | EN |
| Ex. 11-1 | 4.2 | 26.29 | 750 | 2.07 | 3.99 | 5.89 |
| Ex. 11-2 | 4.3 | 24.61 | 740 | 2.24 | 4.22 | 6.23 |

| | | AGED (100 deg. C./22 hrs) | | | | |
|---|---|---|---|---|---|---|
| Compound | Weight | Tensile | EB | M300 | M500 | EN |
| Ex. 11-1 | 4.2 | 27.28 | 700 | 2.18 | 4.65 | 7.5 |
| Ex. 11-2 | 4.3 | 34.43 | 690 | 2.36 | 5.8 | 7.79 |

Analysis of the Results:

The results of Example 11 demonstrate the production of articles (gloves) having excellent properties, produced using sodium aluminate (or other dissolved multivalent metal oxide, hydroxide or salt) in an amount of well below 0.3 phr, in combination with sulphur, sulphur donor(s) and metal cross-linking agent(s) as the second cross-linking agent(s) (i.e. the only secondary cross-linking agents). Between the two trials, the amount of sodium aluminate differed by 0.02 phr. However, the most influencing factor was found to be sulphur and the sulphur-donor ZDBC for the before-aging results. In the case of the post-aged product, the tensile values of Example 11-2 increased considerably. While there can be variation in the individual gloves produced in accordance with these compositions, based on average values calculated from a sample of at least 10 gloves, the amounts of components indicated in this Example have been selected for their suitability for commercial products based on the given combination of cross-linking agents.

Comparative Example 12—Unsuccessful Trials

Several trials were performed prior to identifying the new compositions and methods of the invention to try to incorporate multivalent metals into synthetic polymers in new and effective ways. The techniques attempted included:
  Adding aluminium oxide in solid form to an aqueous suspension of carboxylated synthetic rubber (Nantex 6772). Poor film properties were obtained, with respect to strength, modulus, elongation, softness and feel, for additions up to 5 phr. Based on the understanding since developed, it is understood that when added in a solid form without solubilisation, the aluminium-based cross-linking agent is not as effective. The agent is not sufficiently available for cross-linking with the carbon/late groups.
  Attempting to dissolve zinc oxide in solution for addition in a solubilised form. The techniques attempted to solubilise the zinc oxide were not effective. The unsuccessful techniques included adding sodium hydroxide and heating. To achieve the formation of zinc-based negatively-charged complex ions, a different source of zinc is required and/or different solubilising conditions.
  Adding sodium aluminate directly to an aqueous suspension of carboxlated synthetic rubber emulsion (NANTEX 6772). This resulted in micro-coagulam (i.e. localised immediate cross-linking), and even gelling of the entire emulsion.
  Forming a simple solution of sodium aluminate, and storing prior to usage. When added to an aqueous suspension of carboxylated synthetic rubber emulsion, micro-coagulam was created. It was concluded that that the sodium aluminate had recrystallized upon storage. This was evident from the micro-coagulam formation and the appearance of a residual fine material in the storage vessel.

Example 13—Microscopic Data

Two films were produced from the latex compositions set out in the following table. It is noted that the composition of 13-2 differs from that of 13-1 in that it contains $TiO_2$ to provide whiteness and opaqueness. A cross-section was investigated through a scanning electron microscope and images taken. The elemental composition (C, Al, O, Ti) was analysed at a focussed spot using SEM. This revealed that aluminium could not be detected in the image for the film 13-1, even at high magnification, due to the aluminium atoms being obscured by the carbon of the elastomeric film. This indicates that the aluminium has been deeply and completely incorporated into the film structure, at the intra-particle and inter-particle level.

|  | Composition in phr | |
| --- | --- | --- |
| Experiment No | 13-1 | 13-2 |
| Polymer | 100 | 100 |
| KOH | 1.7 | 1.7 |
| SDBS-Surfactant | 0.3 | 0.3 |
| SLES-Surfactant | 0.3 | 0.3 |
| TiO2 | 0 | 3 |
| Sodium aluminate | 0.15 | 0.15 |
| NaOH | 0.15 | 0.15 |
| KOH (for crosslinker solution) | 0.15 | 0.15 |
| Glycerin | 0.15 | 0.15 |

FIGS. 1-5 contain the images of the two films produced by a scanning electron microscope.

FIGS. 1, 2 and 5 relate to the composition of Example 13-2 (previously numbered Example 9-2). In FIGS. 1 and 2, one peak possibly omitted was at 2.051 keV. FIG. 1 shows a cluster of white particles, being $TiO_2$ particles, indicative of a non-solubilised metal oxide component (a pigment, rather than a cross-linking agent). The magnification in FIG. 1 is 15,000× magnification, with the scale bar indicated representing a distance of about 200 nm. FIG. 2 is of the same image at a different degree of magnification (5,000×, with the scale bar representing 1 μm). FIG. 5 is the same image but focusing on a different section, showing further clusters of white $TiO_2$ particles. The magnification is 25,000×, and the scale bar represents 300 nm.

The elements analysed in the SEM image for the Example 13-2 product were C, O, Al and Ti. In processing, all elements indicated were analysed (normalised). There was one iteration. These are based on standards for each element which were as follows:
Carbon: $CaCO_3$
Oxygen: $SiO_2$
Aluminium: $Al_2O_3$
Titanium: Ti The % amounts of each detected for the composition of Example 13-2, based on atomic % amounts, were as follows:

| Element | Weight % | Atomic % |
| --- | --- | --- |
| C K | 34.05 | 50.59 |
| O K | 33.05 | 36.86 |
| Al K | 1.01 | 0.67 |
| Ti K | 31.88 | 11.88 |
| Totals | 100.00 | |

In the results in the table above, the SEM was focussed on a very small area, roughly 0.2 micron×0.2 micron width, where a cluster of undispersed $TiO_2$ was found. The higher than expected Aluminium amount was due to the adherence of Aluminium to the $TiO_2$ cluster. In normal cured elastomeric areas, the aluminium could not be detected.

FIGS. 3 and 4 relate to the product of Example 13-1. In FIGS. 3 and 4, no peaks were omitted. FIG. 3 shows a uniform surface with proper and even distribution of the aluminium inside the elastomeric matrix. The visible dents are surface undulations. The magnification in FIG. 3 is 25,000×, with the scale bar indicated representing a distance of about 200 nm. FIG. 4 is of the same image at a different degree of magnification (15,000× magnification, with the scale bar representing 200 nm).

The elements analysed were C, O, Al and Ti. In processing, all elements indicated were analysed (normalised) and those detected are indicated in the table below. There were 2 iterations. The elemental analysis was based on the following standards:
Carbon: $CaCO_3$
Oxygen: $SiO_2$ The % amounts of each detected for the composition of Example 13-1, based on atomic amounts, were as follows:

| Element | Weight % | Atomic % |
| --- | --- | --- |
| C K | 88.71 | 91.28 |
| O K | 11.29 | 8.72 |
| Totals | 100.00 | |

Items:
1. A synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0.

1(i) A synthetic elastomeric article comprising the cured product of a synthetic latex composition, the synthetic latex composition comprising a synthetic carboxylated polymer and a cross-linking composition, the cross-linking composition comprising an aqueous solution of a multimetal oxide of the multivalent metal, a hydroxide of the multivalent metal, or a salt of the multivalent metal producing an aqueous solution of negatively charged multivalent metal complex ion having a pH of at least 9.0, in which the amount of the multimetal oxide of the multivalent metal, the hydroxide of the multivalent metal, or the salt of the multivalent metal is less than 0.3 phr.

1(ii). A synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0, the synthetic latex composition further comprising a second cross-linking agent comprising either (a) sulphur and a sulphur donor, (b) a multivalent metal oxide or ionic cross-linking agent, (c) sulphur, a sulphur donor and an ionic cross-linking agent, or (d) sulphur donor.

1(iii). A synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0, wherein the article is a glove having an average thickness of 0.2 mm or less and a modulus at 500% of less than 6.5 MPa.

1(iv). A synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0, the cross-linking composition further comprising a mechanical stabiliser or surfactant, or a combination thereof.

1(v). A synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0, wherein said cross-linking composition comprises a solution of a multimetal oxide of the multivalent metal, a solution of a hydroxide of the multivalent metal, or a solution of a salt of the multivalent metal, which is other than a solution of sodium aluminate.

1(vi). A synthetic elastomeric article comprising the cured product of a synthetic latex composition, the synthetic latex composition comprising a synthetic carboxylated polymer and a cross-linking composition, the cross-linking composition comprising an aqueous solution of a negatively charged multivalent metal complex ion having a pH of at least 9.0, wherein at least one of the following applies:
  i. the cross-linking composition comprises an aqueous solution of a multimetal oxide of the multivalent metal, a hydroxide of the multivalent metal, or a salt of the multivalent metal, such as sodium aluminate, in an amount of less than 0.3 phr of the multimetal oxide of the multivalent metal, the hydroxide of the multivalent metal, or the salt of the multivalent metal;
  ii. the synthetic latex composition comprises a second cross-linking agent comprising sulphur and a sulphur donor;
  iii. the synthetic latex composition comprises a second cross-linking agent comprising a multivalent metal oxide or ionic cross-linking agent;
  iv. the synthetic latex composition comprises a second cross-linking agent comprising sulphur, a sulphur donor and an ionic cross-linking agent;
  v. the synthetic latex composition comprises a second cross-linking agent comprising a sulphur donor;
  vi. the cross-linking composition comprises a mechanical stabiliser and/or surfactant;
  vii. the cross-linking composition comprises a solution of a multimetal oxide of the multivalent metal, a solution of a hydroxide of the multivalent metal, or a solution of a salt of the multivalent metal, which is other than a solution of sodium aluminate;
  viii. the article is a glove having an average thickness of 0.2 mm or less and a modulus at 500% of less than 6.5 MPa.

2. The synthetic elastomeric article of any of items 1 to 1(vi), wherein the synthetic carboxylated polymer comprises synthetic carboxylated polymer particles, and in the cured product the synthetic carboxylated polymer particles are bonded to each other through intra-polymer particle multivalent metal cross-links and inter-polymer particle multivalent metal cross-links, in which the intra-polymer particle and inter-polymer particle multivalent metal cross-links are uniformly distributed throughout the cured product.

3. The synthetic elastomeric article of item 1 or item 2, having a modulus at 500% of less than 7 MPa.

4. The synthetic elastomeric article of any one of items 1 to 3, having an elongation at break of at least 700%.

5. The synthetic elastomeric article of item 1 or item 2, having a modulus at 500% of less than 7 MPa and an elongation at break of at least 700%.

6. The synthetic elastomeric article of any one of the preceding items, wherein the article is in the form of a film.

7. The synthetic elastomeric article of any one of the preceding items, wherein the article is a glove.

8. The synthetic elastomeric article of any one of the preceding items, wherein the multivalent metal of the negatively-charged multivalent metal complex ion is an amphoteric metal.

9. The synthetic elastomeric article of any one of the preceding items, wherein the multivalent metal of the negatively-charged multivalent metal complex ion is selected from the group consisting of aluminium, beryllium, chromium, iron, cobalt, copper, zinc, lead, tin and bismuth.

10. The synthetic elastomeric article of any one of the preceding claims, wherein the multivalent metal of the negatively-charged multivalent metal complex ion is aluminium.

11. The synthetic elastomeric article of any one of the preceding items, wherein the cross-linking composition comprises a solution in water at a pH of at least of 9.0 of a multimetal oxide of the multivalent metal, a hydroxide of the multivalent metal or a salt of the multivalent metal.

12. The synthetic elastomeric article of item 11, wherein the cross-linking composition comprises a solution of the multimetal oxide of the multivalent metal or a solution of the multivalent metal hydroxide.

13. The synthetic elastomeric article of any one of the preceding items, wherein the cross-linking composition comprises a solution of sodium aluminate producing negatively-charged aluminium complex ions.

14. The synthetic elastomeric article of any one of the preceding items, wherein the cross-linking composition comprises alkali.

15. The synthetic elastomeric article of item 14, wherein the cross-linking composition comprises sodium hydroxide, potassium hydroxide or ammonium hydroxide.

16. The synthetic elastomeric article of any one of the preceding items, wherein the cross-linking composition comprises a stabiliser for maintaining the negatively-charged multivalent metal complex ions in solution.

17. The synthetic elastomeric article of item 16, wherein the stabiliser is selected from the group consisting of glycerine, maltodextrin, polysaccharide, polyglycerol and mixtures thereof.

18. The synthetic elastomeric article of any one of the preceding items, wherein the amount of multivalent metal in the synthetic latex composition is 0.01-5 phr.

19. The synthetic elastomeric article of any one of the preceding items, wherein the amount of multivalent metal in the synthetic latex composition is 0.01-0.5 phr.

20. The synthetic elastomeric article of any one of the preceding items, wherein the synthetic carboxylated polymer is selected from the group consisting of carboxylated nitrile butadiene rubber, carboxylated styrene butadiene rubber, carboxylated butyl rubber, carboxylated acrylic butadiene rubber, carboxylated polyisoprene, carboxylated polychloroprene, and mixtures or copolymers thereof.

21. The synthetic elastomeric article of any one of the preceding items, wherein the synthetic carboxylated polymer is carboxylated acrylonitrile butadiene rubber.

22. The synthetic elastomeric article of any one of the preceding items, comprising a second cross-linking agent.

23. The synthetic elastomeric article of item 22, wherein the second cross-linking agent is incorporated into the latex composition in solid form.

24. The synthetic elastomeric article of item 22 or item 23, wherein the second cross-linking agent comprises sulphur, a sulphur donor, or a combination thereof.

25. The synthetic elastomeric article of item 24, wherein sulphur is included in the latex composition in an amount of 0.1-5.5 phr.

26. The synthetic elastomeric article of item 24 or item 25, wherein a sulphur donor is included in the latex composition in an amount of 0.1-4.0 phr.

27. The synthetic elastomeric article of any one of items 22 to items 26, wherein the second cross-linking agent comprises an organic cross-linking agent.

28. The synthetic elastomeric article of item 27, wherein the organic cross-linking agent is present in the latex composition in an amount of 0.1-4.0 phr.

29. The synthetic elastomeric article of any one of items 22 to 28, wherein the second cross-linking agent comprises an ionic cross-linking agent selected from the group consisting of zinc oxide, magnesium oxide and combinations thereof.

30. The synthetic elastomeric article of item 29, wherein the amount of ionic cross-linking agent in the latex composition is 0.1-4.0 phr.

31. An elastomeric article-forming composition comprising:
   a synthetic carboxylated polymer, and
   a cross-linking composition, the cross-linking composition comprising an aqueous solution of a negatively-charged multivalent metal complex ion having a pH of at least 9.0.

31(i) An elastomeric article-forming composition comprising:
   a synthetic carboxylated polymer, and
   a cross-linking composition, the cross-linking composition comprising an aqueous solution of a multimetal oxide of the multivalent metal, a hydroxide of the multivalent metal, or a salt of the multivalent metal, producing a negatively-charged multivalent metal complex ion, and having a pH of at least 9.0, in which the amount of the multimetal oxide of the multivalent metal, the hydroxide of the multivalent metal, or the salt of the multivalent metal is less than 0.3 phr.

31(ii). An elastomeric article-forming composition comprising:
   a synthetic carboxylated polymer,
   a cross-linking composition, the cross-linking composition comprising an aqueous solution of a negatively-charged multivalent metal complex ion having a pH of at least 9.0, and
   a second cross-linking agent comprising either (a) sulphur and a sulphur donor, (b) a multivalent metal oxide or ionic cross-linking agent, (c) sulphur, a sulphur donor and an ionic cross-linking agent, or (d) sulphur donor.

31(iii). An elastomeric article-forming composition comprising:
   a synthetic carboxylated polymer, and
   a cross-linking composition, the cross-linking composition comprising an aqueous solution of a negatively-charged multivalent metal complex ion having a pH of at least 9.0,
wherein the composition can form gloves having an average thickness of 0.2 mm or less and a modulus at 500% of less than 6.5 MPa.

31(iv). An elastomeric article-forming composition comprising:
   a synthetic carboxylated polymer, and
   a cross-linking composition, the cross-linking composition comprising an aqueous solution of a negatively-charged multivalent metal complex ion having a pH of at least 9.0, and a mechanical stabiliser and/or surfactant.

31(v). An elastomeric article-forming composition comprising:
   a synthetic carboxylated polymer, and
   a cross-linking composition, the cross-linking composition comprising an aqueous solution of a multimetal oxide of the multivalent metal, a solution of a hydroxide of the multivalent metal or a solution of a salt of the multivalent metal, which is other than a solution of sodium aluminate, producing a negatively-charged multivalent metal complex ion having a pH of at least 9.0.

31(vi). An elastomeric article-forming composition comprising:
   a synthetic carboxylated polymer, and
   a cross-linking composition, the cross-linking composition comprising an aqueous solution of a negatively-charged multivalent metal complex ion having a pH of at least 9.0, wherein at least one of the following applies:
   i. the cross-linking composition comprises an aqueous solution of a multimetal oxide of the multivalent metal, a hydroxide of the multivalent metal, or a salt of the multivalent metal, such as sodium aluminate, in an amount relative to the synthetic carboxylated polymer to provide at least 0.01 phr and less than 0.3 phr of the multimetal oxide of the multivalent metal, the hydroxide of the multivalent metal, or the salt of the multivalent metal;
   ii. the composition further comprises a second cross-linking agent comprising sulphur and a sulphur donor;
   iii. the composition further comprises a second cross-linking agent comprising a multivalent metal oxide or ionic cross-linking agent;
   iv. the composition further comprises a second cross-linking agent comprising sulphur, a sulphur donor and an ionic cross-linking agent;
   v. the composition further comprises a second cross-linking agent comprising a sulphur donor;
   vi. the cross-linking composition comprises a mechanical stabiliser and/or surfactant;
   vii. the cross-linking composition comprises a solution of a multimetal oxide of the multivalent metal, a solution of a hydroxide of the multivalent metal, or a solution of a salt of the multivalent metal, which is other than a solution of sodium aluminate;
   viii. the composition can form gloves having an average thickness of 0.2 mm or less and a modulus at 500% of less than 6.5 MPa.

32. The elastomeric article-forming composition of any one of items 31 to 31(vi), wherein the multivalent metal of the negatively-charged multivalent metal complex ion is an amphoteric metal.

33. The elastomeric article-forming composition of any one of items 31 to 32, wherein the multivalent metal of the negatively-charged multivalent metal complex ion is selected from the group consisting of aluminium, beryllium, chromium, iron, cobalt, copper, zinc, lead, tin and bismuth.

34. The elastomeric article-forming composition of any one of items 31 to 33, wherein the multivalent metal of the negatively-charged multivalent metal complex ion is aluminium.

35. The elastomeric article-forming composition of any one of items 31 to 34, wherein the cross-linking composition comprises a solution in water at a pH of at least of 9.0 of a multimetal oxide of the multivalent metal, a hydroxide of the multivalent metal or a salt of the multivalent metal.

36. The elastomeric article-forming composition of item 35, wherein the cross-linking composition comprises a solution of the multimetal oxide of the multivalent metal or a solution of the multivalent metal hydroxide.

37. The elastomeric article-forming composition of any one of items 31 to 36, wherein the cross-linking composition comprises a solution of sodium aluminate producing negatively-charged aluminium complex ions.

38. The elastomeric article-forming composition of any one of items 31 to 37, wherein the cross-linking composition comprises alkali.

39. The elastomeric article-forming composition of item 38, wherein the cross-linking composition comprises sodium hydroxide, potassium hydroxide or ammonium hydroxide.

40. The elastomeric article-forming composition of any one of items 31 to 39, wherein the cross-linking composition comprises a stabiliser for maintaining the negatively-charged multivalent metal complex ions in solution.

41. The elastomeric article-forming composition of item 40, wherein the stabiliser is selected from the group consisting of glycerine, maltodextrin, polysaccharide, polyglycerol and mixtures thereof.

42. The elastomeric article-forming composition of any one of items 31 to 41, wherein the amount of multivalent metal in the composition is 0.01-5 phr.

43. The elastomeric article-forming composition of any one of items 31 to 42, wherein the amount of multivalent metal in the composition is 0.01-0.5 phr.

44. The elastomeric article-forming composition of any one of items 31 to 43, wherein the synthetic carboxylated polymer is selected from the group consisting of carboxylated nitrile butadiene rubber, carboxylated styrene butadiene rubber, carboxylated butyl rubber, carboxylated acrylic butadiene rubber, carboxylated polyisoprene, carboxylated polychloroprene, and mixtures or copolymers thereof.

45. The elastomeric article-forming composition of any one of items 31 to 44, wherein the synthetic carboxylated polymer is carboxylated acrylonitrile butadiene rubber.

46. The elastomeric article-forming composition of any one of items 31 to 45, comprising a second cross-linking agent.

47. The elastomeric article-forming composition of item 46, wherein the second cross-linking agent is in solid form.

48. The elastomeric article-forming composition of item 46 or item 47, wherein the second cross-linking agent comprises sulphur, a sulphur donor, or a combination thereof.

49. The elastomeric article-forming composition of item 48, wherein sulphur is included in the composition in an amount of 0.1-5.5 phr.

50. The elastomeric article-forming composition of item 48 or item 49, wherein a sulphur donor is included in the latex composition in an amount of 0.1-4.0 phr.

51. The elastomeric article-forming composition of any one of items 46 to 50, wherein the second cross-linking agent comprises an organic cross-linking agent.

52. The elastomeric article-forming composition of item 51, wherein the organic cross-linking agent is present in the composition in an amount of 0.1-4.0 phr.

53. The elastomeric article-forming composition of any one of items 46 to 52, wherein the second cross-linking agent comprises an ionic cross-linking agent selected from the group consisting of zinc oxide, magnesium oxide and combinations thereof.

54. The elastomeric article-forming composition of item 53, wherein the amount of ionic cross-linking agent in the composition is 0.1-4.0 phr.

55. A method of manufacturing a synthetic elastomeric article comprising:
adding a cross-linking composition comprising an aqueous solution of a negatively-charged multivalent metal complex ion having a pH of at least 9.0 to an aqueous suspension of a synthetic carboxylated polymer having a pH of at least 9.0 to produce a synthetic latex composition;
forming the synthetic latex composition into the shape of the synthetic elastomeric article; and
curing the synthetic latex composition to form the synthetic elastomeric article.

55(i). A method of manufacturing a synthetic elastomeric article comprising:
adding a cross-linking composition having a pH of at least 9.0 and comprising an aqueous solution of a multimetal oxide of the multivalent metal, a hydroxide of the multivalent metal, or a salt of the multivalent metal, which solution contains negatively-charged multivalent metal complex ions, to an aqueous suspension of a synthetic carboxylated polymer having a pH of at least 9.0, in an amount to provide less than 0.3 phr of the multimetal oxide of the multivalent metal, the hydroxide of the multivalent metal, or the salt of the multivalent metal, to produce a synthetic latex composition;
forming the synthetic latex composition into the shape of the synthetic elastomeric article; and
curing the synthetic latex composition to form the synthetic elastomeric article.

55(ii). A method of manufacturing a synthetic elastomeric article comprising:
adding (i) a cross-linking composition comprising an aqueous solution of a negatively-charged multivalent metal complex ion having a pH of at least 9.0 and (ii) a second cross-linking agent comprising either: (a) sulphur and a sulphur donor, (b) a multivalent metal oxide or ionic cross-linking agent, (c) sulphur, a sulphur donor and an ionic cross-linking agent, or (d) sulphur donor, to an aqueous suspension of a synthetic carboxylated polymer having a pH of at least 9.0 to produce a synthetic latex composition;
forming the synthetic latex composition into the shape of the synthetic elastomeric article; and
curing the synthetic latex composition to form the synthetic elastomeric article.

55(iii). A method of manufacturing a synthetic elastomeric article comprising:
adding a cross-linking composition comprising an aqueous solution of a negatively-charged multivalent metal complex ion having a pH of at least 9.0 to an aqueous suspension of a synthetic carboxylated polymer having a pH of at least 9.0 to produce a synthetic latex composition;
forming the synthetic latex composition into the shape of the synthetic elastomeric article; and curing the synthetic latex composition to form gloves having an average thickness of 0.2 mm or less and a modulus at 500% of less than 6.5 MPa.

55(iv). A method of manufacturing a synthetic elastomeric article comprising:
adding a cross-linking composition comprising an aqueous solution of a negatively-charged multivalent metal complex ion having a pH of at least 9.0 and a mechanical stabiliser and/or surfactant, to an aqueous suspension of a synthetic carboxylated polymer having a pH of at least 9.0 to produce a synthetic latex composition;
forming the synthetic latex composition into the shape of the synthetic elastomeric article; and
curing the synthetic latex composition to form the synthetic elastomeric article, 55(v). A method of manufacturing a synthetic elastomeric article comprising:
adding a cross-linking composition having a pH of at least 9.0 and comprising an aqueous solution of multimetal oxide of the multivalent metal, a solution of a hydroxide of the multivalent metal, or a solution of a salt of the multivalent metal, which is other than a solution of sodium aluminate, which solution contains negatively-charged multivalent metal complex ions, to an aqueous suspension of a synthetic carboxylated polymer having a pH of at least 9.0, to produce a synthetic latex composition;
forming the synthetic latex composition into the shape of the synthetic elastomeric article; and
curing the synthetic latex composition to form the synthetic elastomeric article, 55(vi) A method of manufacturing a synthetic elastomeric article comprising:
adding a cross-linking composition comprising an aqueous solution of a negatively-charged multivalent metal complex ion having a pH of at least 9.0 to an aqueous suspension of a synthetic carboxylated polymer having a pH of at least 9.0 to produce a synthetic latex composition;
forming the synthetic latex composition into the shape of the synthetic elastomeric article; and
curing the synthetic latex composition to form the synthetic elastomeric article,
wherein at least one of the following applies:
i. the cross-linking composition comprises an aqueous solution of a multimetal oxide of the multivalent metal, a hydroxide of the multivalent metal, or a salt of the multivalent metal, and is added in an amount to provide less than 0.3 phr of the multimetal oxide of the multivalent metal, the hydroxide of the multivalent metal, or the salt of the multivalent metal;
ii. a second cross-linking agent comprising sulphur and a sulphur donor is added to the synthetic carboxylated polymer;
iii. a second cross-linking agent comprising a multivalent metal oxide or ionic cross-linking agent is added to the synthetic carboxylated polymer;
iv. a second cross-linking agent comprising sulphur, a sulphur donor and an ionic cross-linking agent is added to the synthetic carboxylated polymer;
v. a second cross-linking agent comprising a sulphur donor is added to the synthetic carboxylated polymer;
vi. the cross-linking composition comprises a mechanical stabiliser and/or surfactant;
vii. the cross-linking composition comprises a solution of a multimetal oxide of the multivalent metal, a solution of a hydroxide of the multivalent metal, or a solution of a salt of the multivalent metal, which is other than a solution of sodium aluminate;
viii. the synthetic latex composition is cured to form gloves having an average thickness of 0.2 mm or less and a modulus at 500% of less than 6.5 MPa.

56. The method of any one of items 55 to 55(vi), wherein the cross-linking composition is added sufficiently slowly to the aqueous suspension of synthetic carboxylated polymer to avoid localised coagulation due to pH shock.

57. The method of item 56, wherein the pH of the cross-linking composition is within 1.0 units of the pH of the aqueous suspension of the synthetic carboxylated polymer.

58. The method of any one of items 55 to 57, comprising adding alkali to the aqueous suspension of the synthetic carboxylated polymer prior to the addition of the cross-linking composition to raise the pH of the aqueous suspension to at least 9.0.

59. The method of any one of items 55 to 58, comprising adding the cross-linking composition to the aqueous suspension of the synthetic carboxylated polymer when the concentration of multivalent metal ions in the cross-linking composition is between about 1% and 10% by weight of the cross-linking composition.

60. The method of any one of items 55 to 59, comprising adding the cross-linking composition in an amount of between about 1 and 20 parts per 100 parts by volume of the aqueous suspension of the synthetic carboxylated polymer.

61. The method of any one of items 55 to 60, comprising adding surfactant to the aqueous suspension of synthetic carboxylated polymer together with the cross-linking composition.

62. The method of any one of items 55 to 61, wherein the step of forming the latex composition into the shape of the synthetic elastomeric article comprises a dipping a former into the latex composition.

63. The method of item 62, wherein the former is a glove-shaped former, and the method is for the manufacture of a glove.

64. The method of item 62 or item 63, comprising dipping the former into a coagulant composition prior to the step of dipping the former into the latex composition.

65. The method of any one of items 55 to 64, wherein the multivalent metal of the negatively-charged multivalent metal complex ion is an amphoteric metal.

66. The method of any one of items 55 to 65, wherein the multivalent metal of the negatively-charged multivalent metal complex ion is aluminium.

67. The method of any one of items 55 to 66, comprising adding the cross-linking composition to the aqueous suspension of the synthetic carboxylated polymer in an amount to provide 0.01-5 phr of multivalent metal in the latex composition.

68. The method composition of any one of items 55 to 67, comprising adding the cross-linking composition to the aqueous suspension of the synthetic carboxylated polymer in an amount to provide 0.01-0.5 phr of multivalent metal in the latex composition.

69. The method of any one of items 55 to 68, comprising forming the cross-linking composition by solubilising a multimetal oxide of the multivalent metal, a hydroxide of the multivalent metal or a salt of the multivalent metal in water, and controlling the pH to be at least 9.0.

70. The method of item 69, comprising forming the cross-linking composition by solubilising sodium aluminate in water with heating.

71. The method of item 69 or item 70, wherein the step of forming the cross-linking composition comprises adding an alkali to raise the pH of the cross-linking composition to at least 9.0.

72. The method of any one of items 69 to 71, comprising adding a stabiliser to the cross-linking composition to maintain the multivalent metal complex ions in solution, to form a stabilised cross-linking composition, prior to addition of the cross-linking composition to the aqueous suspension of synthetic carboxylated polymer.

73. The method of item 72, wherein the stabiliser is selected from the group consisting of glycerin, maltodextrin, polysaccharide, polyglycerol and mixtures thereof.

74. The method of any one of items 69 to 73, comprising a step of diluting the cross-linking composition to obtain a multivalent metal ion concentration of between 1-10% by weight of the cross-linking composition, prior to the addition of the cross-linking composition to the aqueous suspension of a synthetic carboxylated polymer.

75. The method of any one of items 55 to 74, wherein the synthetic carboxylated polymer comprises synthetic carboxylated polymer particles, and the curing step results in the synthetic carboxylated polymer particles being bonded to each other through intra-polymer particle multivalent metal cross-links and inter-polymer particle multivalent metal cross-links, in which the intra-polymer particle and inter-polymer particle multivalent metal cross-links are uniformly distributed throughout the cured product.

76. The method of any one of items 55 to 75, wherein the synthetic carboxylated polymer is selected from the group consisting of carboxylated nitrile butadiene rubber, carboxylated styrene butadiene rubber, carboxylated butyl rubber, carboxylated acrylic butadiene rubber, carboxylated polyisoprene, carboxylated polychloroprene, and mixtures or copolymers thereof.

77. The method of any one of items 55 to 44, wherein the synthetic carboxylated polymer is carboxylated acrylonitrile butadiene rubber.

78. The method of any one of items 55 to 77, comprising adding to the latex composition particulate components selected from the group consisting of second cross-linking agents, plasticizers, anti-ozonants, stabilisers such as pH stabilisers, emulsifiers, antioxidants, vulcanising agents, pigments, fillers, colourising agents and sensitisers prior to forming the latex composition into the shape of the synthetic elastomeric article.

79. The method of item 78, wherein the particulate components comprise a second cross-linking agent.

80. The method of item 79, wherein the second cross-linking agent comprises sulphur, a sulphur donor, or a combination thereof.

81. The method of item 80, wherein sulphur is added into the latex composition in an amount of 0.1-5.5 phr.

82. The method of item 80 or item 81, wherein a sulphur donor is added into the latex composition in an amount of 0.1-4.0 phr.

83. The method of any one of items 79 to 82, wherein the second cross-linking agent comprises an organic cross-linking agent.

84. The method of item 83, wherein the organic cross-linking agent is added to the latex composition in an amount of 0.1-4.0 phr.

85. The method of any one of items 79 to 84, wherein the second cross-linking agent comprises an ionic cross-linking agent selected from the group consisting of zinc oxide, magnesium oxide and combinations thereof.

86. The method of item 53, wherein the ionic cross-linking agent is added into the latex composition in an amount of 0.1-4.0 phr.

87. An elastomeric article produced from the elastomeric article-forming composition of any one of items 31 to 54 or by the method of any one of items 55 to 86.

88. Elastomeric gloves produced from the elastomeric film-forming composition of any one of items 31 to 54 or by the method of any one of items 55 to 86.

89. A synthetic elastomeric article comprising cured synthetic carboxylated polymer particles bonded to each other through intra-polymer particle multivalent metal cross-links and inter-polymer particle multivalent metal cross-links, in which the intra-polymer particle and inter-polymer particle multivalent metal cross-links are uniformly distributed throughout the cured product.

90. The synthetic elastomeric article of item 89, and comprising the features of any one of items 1 to 30.

The invention claimed is:

1. A synthetic elastomeric article comprising the cured product of a synthetic latex composition,
wherein the synthetic latex composition comprises a synthetic carboxylated polymer, a cross-linking composition, and a second cross-linking agent,
wherein the synthetic latex composition is prepared by:
adding the cross-linking composition and the second cross-linking agent to an aqueous suspension of the synthetic carboxylated polymer to obtain the synthetic latex composition,
wherein the cross-linking composition comprises an aqueous solution of a negatively charged multivalent metal complex ion having a pH of at least 9.0, a source of the multivalent metal in the negatively charged multivalent metal complex ion being (a) a multimetal oxide of the multivalent metal, (b) a hydroxide of the multivalent metal, or (c) a salt of the multivalent metal,
wherein the cross-linking composition further comprises at least one of sodium hydroxide, potassium hydroxide, and ammonium hydroxide to provide pH control to stabilise the aqueous solution of the negatively charged multivalent metal complex ion, and
wherein the second cross-linking agent comprises either (a) sulphur in an amount of not more than 1.0 phr and a sulphur donor in an amount of not more than 1.0 phr, (b) a multivalent metal oxide or ionic cross-linking agent in an amount of not more than 0.3 phr, (c) sulphur in an amount of not more than 1.0 phr, a sulphur donor in an amount of not more than 1.0 phr, and an ionic cross-linking agent in an amount of not more than 1.0 phr, or (d) sulphur donor in an amount of not more than 1.0 phr.

2. The synthetic elastomeric article of claim 1, wherein the synthetic carboxylated polymer comprises synthetic carboxylated polymer particles, and in the cured product the synthetic carboxylated polymer particles are bonded to each other through intra-polymer particle multivalent metal cross-links and inter-polymer particle multivalent metal cross-links, in which the intra-polymer particle and inter-polymer particle multivalent metal cross-links are uniformly distributed throughout the cured product.

3. The synthetic elastomeric article of claim 1, having a modulus at 500% of less than 6.5 MPa.

4. The synthetic elastomeric article of claim 1, wherein the article is a glove.

5. The synthetic elastomeric article of claim 1, wherein the multivalent metal of the negatively-charged multivalent metal complex ion is aluminium.

6. The synthetic elastomeric article of claim 1, wherein the cross-linking composition comprises a solution of sodium aluminate producing negatively-charged aluminium complex ions.

7. The synthetic elastomeric article of claim 1, wherein the amount of multivalent metal in the synthetic latex composition is 0.01-0.5 phr.

8. The synthetic elastomeric article of claim 1, wherein the second cross-linking agent comprises (a) sulphur and a sulphur donor, and is free of solid multivalent metal oxide.

9. The synthetic elastomeric article of claim 1, wherein the second cross-linking agent comprises (b) a multivalent metal oxide or ionic cross-linking agent, and is free of sulphur and sulphur donors.

10. The synthetic elastomeric article of claim 1, wherein the second cross-linking agent comprises (d) a sulphur donor, and is free of sulphur and solid multivalent metal oxide.

11. The synthetic elastomeric article of claim 1, wherein the total amount of all second cross-linking agents is not more than 1.0 phr.

12. The synthetic elastomeric article of claim 1, wherein the cross-linking composition comprises a solution of sodium aluminate producing negatively-charged aluminium complex ions, and wherein an amount of the sodium aluminate is 0.01-0.5 phr.

13. The synthetic elastomeric article of claim 12, wherein a total amount of the second cross-linking agent is not more than 1.0 phr.

14. The synthetic elastomeric article of claim 12, wherein the cross-linking composition comprises a mechanical stabilizer.

15. The synthetic elastomeric article of claim 14, wherein an amount of the mechanical stabilizer in the cross-linking composition is 0.03-15 phr.

16. The synthetic elastomeric article of claim 12, wherein the cross-linking composition comprises a mechanical stabilizer selected from the group consisting of water-soluble or water-miscible organic polyols and water soluble or water-miscible thickening agents.

17. The synthetic elastomeric article of claim 16, wherein the mechanical stabilizer is selected from the group consisting of glycerine, sugars, sugar alcohols, maltodextrin, polysaccharide, polyglycerol, polyethylene glycols, starch, modified starch, and mixtures thereof.

18. The synthetic elastomeric article of claim 1, wherein the cross-linking composition comprises not more than 20% by weight of an insoluble precipitate of the multivalent metal.

19. The synthetic elastomeric article of claim 1, wherein the cross-linking composition comprises not more than 5% by weight of an insoluble precipitate of the multivalent metal.

20. The synthetic elastomeric article of claim 1, wherein a total amount of the second cross-linking agent is not more than 3.0 phr.

21. The synthetic elastomeric article of claim 12, wherein a total amount of the second cross-linking agent is not more than 3.0 phr.

22. The synthetic elastomeric article of claim 1, wherein a total amount of the second cross-linking agent is not more than 2.0 phr.

23. The synthetic elastomeric article of claim 12, wherein a total amount of the second cross-linking agent is not more than 2.0 phr.

24. A synthetic elastomeric article comprising the cured product of a synthetic latex composition,
wherein the synthetic latex composition comprises a synthetic carboxylated polymer, a cross-linking composition, and a second cross-linking agent,
wherein the synthetic latex composition is prepared by:
adding the cross-linking composition and the second cross-linking agent to an aqueous suspension of the synthetic carboxylated polymer to obtain the synthetic latex composition,
wherein the cross-linking composition comprises an aqueous solution of 0.01-0.9 phr of an aluminium source and 0.1-5.0 phr of alkali hydroxide producing a negatively charged aluminium complex ion having a pH of at least 9.0, the aluminium source being (a) a multimetal oxide of aluminium, (b) a hydroxide of aluminium, or (c) a salt of aluminium, and
wherein the second cross-linking agent comprises either (a) sulphur and a sulphur donor, (b) a multivalent metal oxide or ionic cross-linking agent, (c) sulphur, a sulphur donor and an ionic cross-linking agent, or (d) sulphur donor.

25. The synthetic elastomeric article of claim 24, wherein the article is a glove.

26. The synthetic elastomeric article of claim 25, having a modulus at 500% of less than 6.5 MPa.

27. The synthetic elastomeric article of claim 24, wherein an amount of the aluminium source in the synthetic latex composition is 0.01-0.5 phr.

28. The synthetic elastomeric article of claim 24, wherein the aluminium source is sodium aluminate.

29. A synthetic elastomeric article comprising the cured product of a synthetic latex composition,
wherein the synthetic latex composition comprises a synthetic carboxylated polymer and a cross-linking composition,
wherein the cross-linking composition comprises an aqueous solution of a negatively charged multivalent metal complex ion having a pH of at least 9.0, a source of the multivalent metal in the negatively charged multivalent metal complex ion being (a) a multimetal oxide of the multivalent metal, (b) a hydroxide of the multivalent metal, or (c) a salt of the multivalent metal,
wherein the synthetic latex composition further comprises a second cross-linking agent comprising either (a) sulphur in an amount of not more than 1.0 phr and a sulphur donor in an amount of not more than 1.0 phr, (b) a multivalent metal oxide or ionic cross-linking agent in an amount of not more than 0.3 phr, (c) sulphur in an amount of not more than 1.0 phr, a sulphur donor in an amount of not more than 1.0 phr, and an ionic cross-linking agent in an amount of not more than 1.0 phr, or (d) sulphur donor in an amount of not more than 1.0 phr, and
wherein the cross-linking composition further comprises a mechanical stabiliser selected from the group consisting of glycerine, sugars, sugar alcohols, maltodextrin, polysaccharide, polyglycerol, starch, modified starch, and mixtures thereof.

* * * * *